United States Patent [19]

Marquez et al.

[11] Patent Number: 4,975,434

[45] Date of Patent: Dec. 4, 1990

[54] ANTIVIRAL AND ANTICANCER CYCLOPENTENYL CYTOSINE

[75] Inventors: Victor E. Marquez, Gaithersburg; John S. Driscoll, Rockville, both of Md.; Mu-Ill Lim, Trumbull, Conn.; Christopher K. Tseng, Burtonsville, Md.; Alberto Haces; Robert I. Glazer, both of Gaithersburg, Md.

[73] Assignee: The United States of America as represented by the Secretary of the Department of Health and Human Services, Washington, D.C.

[21] Appl. No.: 307,115

[22] Filed: Jan. 31, 1989

Related U.S. Application Data

[63] Continuation-in-part of Ser. No. 867,583, May 27, 1986, abandoned.

[51] Int. Cl.$^5$ .................... A61K 31/505; A61K 31/52; C07D 239/55; C07D 239/56; C07D 239/28; C07D 239/36; C07D 471/04; C07D 473/00; C07D 473/18; C07D 473/32; C07D 473/40

[52] U.S. Cl. .................... 514/274; 514/241; 514/245; 514/258; 514/261; 514/262; 514/346; 514/348; 514/349; 544/220; 544/223; 544/254; 544/264; 544/314; 544/317; 546/296; 546/297; 546/301; 549/437; 549/438

[58] Field of Search .................... 514/274

[56] References Cited

FOREIGN PATENT DOCUMENTS 61-87674  5/1986  Japan .

OTHER PUBLICATIONS

Ono et al.: Chemical Abstracts 106: 33435f.
Anita et al.: Nucleic Acids Res., Symposium Series 12, 25–28, 1983.
Ohno: Nucleosides & Nucleotides 4(1&2), 21–28, 1985.
Goldin: Eur. J. Cancer, 17, 124–142, 1981.
Venditti: "Pharmacological Basis of Cancer Chemotherapy", 245–270, 1975, The Williams & Wilkins Co., Baltimore.

*Primary Examiner*—Cecilia Shen
*Attorney, Agent, or Firm*—Robert Benson

[57] ABSTRACT

Cyclopentenyl pyrimidine compounds have potent antiviral, anti-tumor and differentiating activity. Of these compounds, cyclopentenyl cytosine has proved to be particularly effective in a variety of tumors, as well as having good antiviral activity and potent differentiating properties.

2 Claims, 1 Drawing Sheet

ANTIVIRAL AND ANTICANCER CYCLOPENTENYL CYTOSINE

This application is a continuation-in-part of Ser. No. 867,593, filed May 27, 1986, now abandoned which application is incorporated herein by reference.

FIELD OF THE INVENTION

The present invention relates to antiviral and cancer chemotherapy and, more particularly, to cyclopentenyl pyrimidines which can be used for antiviral and cancer chemotherapy, as well as to methods of preparation of these compounds.

BACKGROUND OF THE INVENTION

Cancer can be considered to be a group of diseases that can occur in any tissue, organ, or system of the body. The causes of all cancers are not yet known, nor are there any reported major qualitative metabolic differences between cancer cells and host tissue cells of origin. Accordingly, cancer chemotherapy, unlike the chemotherapy of infectious diseases wherein the disease-causing organism itself offers a distinct metabolic or structural biological target, has far more restrictive fundamental concepts on which to pattern therapeutic treatment.

Most known classes of anticancer drugs exert their action principally because of quantitative differences in metabolic rates of production or levels of certain nucleic acids, enzymes, proteins, hormones, metabolic intermediates, etc., rather than because of qualitative biologic differences between cancer cells and normal cells. Thus, anticancer drugs do not exhibit selective toxicity in the classical sense.

Nucleosides, as a specific group of anticancer or antiviral agents, can be taken up selectively into cells via several mechanisms. Once the corresponding nucleotide is formed intracellularly, the nucleotide is then available for conversion into diphosphates, triphosphates, etc., and thereby can exert its cytotoxic effect via a number of possible mechanisms including effects on DNA polymerase, ribonucleoside diphosphate reductase, incorporation into DNA, and inhibition of DNA and cellular metabolism in general.

A number of anticancer nucleosides or bases have been described in the prior art. For example, cytosine arabinoside (ara-C), 5-fluorouracil, 5-fluorodeoxyuridine, 6-mercaptopurine, and thioguanine are among drugs currently used in the clinical treatment of cancer in human patients. Literally scores of pyrimidines, purines, structurally related heterocyclic bases, nucleosides, etc., have been synthesized and demonstrated to possess high cytotoxic activity in cell culture and, in a number of instances, in tumor-bearing animals. However, unfavorable therapeutic indexes have restricted the clinical use of this class of antimetabolites to the relatively few antineoplastic drugs presently used for the chemotherapy of cancer.

Recently, a number of compounds have been reported wherein the oxygen of the furanose ring of a number of natural and synthetic nucleosides has been replaced by a methylene group. This transformation changes the furanose ring into a cyclopentane ring. The term carbocyclic nucleoside is used to describe these compounds which are somewhat structurally analogous to natural and synthetic nucleosides wherein the furanose ring is replaced by a 5-member carbon ring. However, it is perhaps more accurate to refer to these compounds as carbocyclic nucleoside isosteres because, strictly speaking, they are not nucleosides. Carbocyclic nucleosides, however, is a convenient term because these compounds undoubtedly exert their biological activity by mimicking the parent nucleosides, although their activities are different for a variety of reasons.

Consistent with the presence of the carbocyclic ring, they are not subject to the action of nucleoside phosphorylases and hydrolases that cleave normal nucleosides. Conformationally, however, the expected similarity in bond lengths and bond angles between the tetrahydrofuran and cyclopentane rings allows these compounds to behave as substrates or inhibitors of the enzymes that activate and interconvert nucleosides and nucleotides in living cells. As a result of this likeness, many of these compounds possess an interesting range of biological activities, particularly in the areas of antiviral and anticancer chemotherapy. The majority of carbocyclic nucleosides known to date are of synthetic origin, although two of the most active compounds are natural products: aristeromycin and neplanocin A (C-Ado, Formula 5).

Several carbocyclic nucleosides were conceived and synthesized prior to the isolation of the carbocyclic adenosine prototype aristeromycin from natural sources. Some of the initially synthesized compounds were simple cyclopentyl substituted bases, but others included true isosteres of thymidine and adenosine. The first reported synthesis of carbocyclic thymidine however, was found to be in error, but the correct compound was later prepared. Most current synthetic approaches begin with the construction of the heterocyclic base from a functionalized cyclopentylamine which, with very few exceptions, is obtained as a racemic mixture. Consequently, most of the reported synthetic carbocyclic nucleosides are racemates. Recently, however, an enantioselective synthesis of aristeromycin and neplanocin A was achieved by Ohno et al., as reported in *J. Am. Chem. Soc.* 105, 4049 (1983). Of the three total syntheses of neplanocin A reported in 1983, two are enantioselective.

The basic method of synthesis of carbocyclic nucleosides has remained substantially unchanged since Shealy's original work, published in *J. Am. Chem. Soc,* 88, 3884 (1966), and J. Am. Chem. Soc. 91.3075 (1969). This synthesis involves:

(1) synthesis of the carbocyclic ribofuranosylamine (C-rib-NH$_2$), and (2) construction of the purine or pyrimidine ring from this amine by well established procedures in nucleoside chemistry.

The other syntheses that followed differed mainly in the novelty and efficiency of producing the desired C-rib-NH$_2$ with the correct stereochemical disposition of substituents.

Most of the prior syntheses use a rigid bicyclo[2.2.1-]heptene system, which allow for better control of the stereochemistry of incoming substituents in subsequent reactions. When nonbornadienes were used as starting materials, the extra carbon atom in the molecule was replaced by the required amino function via a Hoffmann rearrangement of a carboxylic acid amide generated after ozonolysis of one of the double bonds. Later, in an effort to overcome the use of the Hoffmann reaction, azabicyclo[2.2.1]heptene systems, which already contain a latent amine functionality, allowed a more efficient generation of C-rib-NH$_2$. Ohno's use of a chemico-enzymatic hydrolysis of a mesodiester allowed synthesis of an enantiomerically pure C-rib-NH$_2$. Other methods often led to the desired amine only in its racemic form.

Among the various synthetic approaches to purines and pyrimidines, only a few methods have been used in carbocyclic nucleoside chemistry, mainly because of the early commitment to the synthesis via the cyclopentylamine.

To form purines, the time-honored method used has been to convert the carbocyclic amine to the corresponding pyrimidylaminocyclopentane derivative which is then followed by completion of the pyrrole, imidazole, or triazole ring, to give the corresponding purine carbocyclic nucleoside. The reactive 6-chloro substituent allows replacement with ammonia or water to give the adenine and hypoxanthine analogues, respectively. Completion of the bicyclic system varies accordingly; it consists of (1) a spontaneous acid-catalyzed cyclization; (2) formation of the imidazole ring after treatment with an activated one-carbon reagent such as triethylorthoformate; or (3) diazotization of the primary aromatic amine to give the 8-azapurine analogue.

All reported syntheses of carbocyclic pyrimidines have made use of preformed carbocyclic amines as starting materials. The procedures apply the general methodology for the synthesis of uracil and thymine. An acyl isocyanate derivative is reacted with the carbocyclic amine to give an intermediate acryloylurea which is then cyclized in the presence of concentrated ammonia, or with acid catalysts, to give the uracil or thymine analogue. Alternatively, the same result can be obtained by reacting the carbocyclic amine with 3-ethoxy-N,2-bis(ethoxycarbonyl)acrylamide to give the 5-carboethoxyuracil. The 5-substituent is later removed by hydrolysis and decarboxylation. The generated unsubstituted carbocyclic uridine derivatives are amenable to direct halogenation at C-5 and the halogen is later displaced by a nucleophile to produce a number of 5-substituted uridine analogues.

Transformation of the uracil ring into cytosine requires cnnversion of the cyclic amide to the 4-chloropyrimidine, which reacts with ammonia. Alternatively, thiation of the uridine analogue to the corresponding 4-thiouracil derivative, followed by methylation and ammonolysis, produces identical results.

Purine carbocyclic nucleosides include compounds with an intact imidazo[4,5-d]pyrimidine (purine) ring system bearing different 9-cyclopentyl substituents that mimic the several known sugar moieties of the corresponding nucleoside counterparts. Other variations include substitutions at positions 6, 2, and 8.

The first of the ribose isosteres that was synthesized was the saturated carbocyclic analogue of adenosine, C-Ado. Shealy et al., *J. Am. Chem. Soc.*, 88, 91:3075 (1969). C-Ado displayed a wide range of biological activities. It was highly cytotoxic to both H.Ep.-2 and L1210 cells in culture, but it demonstrated poor selectivity towards the tumor cells in view of its inactivity in the in vivo mouse L1210 model system. At subtoxic concentrations, it induced cell proliferation of quiescent normal cells, but in contrast it inhibited growth in malignant cell lines. The primary toxic effects of C-Ado appear to be mainly derived from the corresponding nucleotide (C-AMP) generated in cells containing adenosine kinase. Like adenosine, C-Ado is also deaminated by adenosine deaminase, but its affinity for the enzyme is a hundredfold lower.

All other 6-substituted C-Ado analogues reported have also been found to be ineffective against L1210 leukemia in mice, despite the fact that some of them were found to be cytotoxic to H.Ep.-2 cells in vitro.

The saturated carbocyclic analogue of 3-deazaadenosine (3-deazaaristeromycin) was first reported in 1982 by Montgomery et al in J. Med. Chem. 25. 626 (1982). This compound was found to be a very potent and specific inhibitor of the enzyme which hydrolyzes S-adenosyl-L-homocysteine (AdoHcy). Besides demonstratinq good antiviral activity against herpes simplex and vaccinia viruses, it was devoid of some of the undesirable side effects typical of other antiviral agents operating by the same mechanism. The antiviral activity observed for these compounds appears to result from the inhibition of methylation of the 5' cap of viral m-RNA caused by the increase accumulation of AdoHcy inside the cell. Antiviral activity of this nature is discussed by DeClerq et al in *Biochem. Biophys Res. Commun.* 129, 306 (1985). Inhibition of this critical methylation reaction hinders the translation of viral m-RNA into viral proteins. A common characteristic shared by 3-deazaadenosine and 3-deazaaristeromycin is resistance towards phosphorylation and deamination, which suggests that the carbocyclic structure plays a significant role in conferring the aforementioned selectivity to 3-deazaaristeromycin.

Recently, a different class of carbocyclic nucleosides has become interesting after the isolation and total synthesis of the fermentation antibiotic neplanocin A. Neplanocin A is also a potent inhibitor of AdoHyc hydrolase, but since it is readily phosphorylated, it has a multiplicity of side effects including cytotoxicity. The important structural feature of neplanocin A is the unsaturation present in its cyclopentenyl ring, which gives the molecule unique pharmacologic properties when compared with its saturated counterpart, aristeriomycin.

SUMMARY OF THE INVENTION

It is an object of the present invention to overcome deficiencies in the prior art, such as indicated above.

A further object is to advance the art of antiviral and cancer chemotherapy.

Still a further object is to provide cyclopentenyl pyrimidines and methods for preparing these compounds.

The present invention relates to cyclopentenyl pyrimidines and methods for preparing and using these compounds. These compounds, particularly cyclopentenyl cytosine, have been found to be particularly potent and active agents against ara-C resistant tumors and human tumors grown in mice. These compounds also have potent antiviral properties both in vitro and in vivo. In addition, these compounds cause cancer cells to differentiate into non-malignant cells.

The compounds of the present invention can readily be synthesized by functionalizing an alcohol of formula 1, then conducting a direct-displacement reaction rather than building the heterocyclic ring stepwise, as described above. The protected compounds obtained from this procedure can then be further manipulated and the protective groups removed to give the biologically active compounds of the present invention.

Of these compounds, cyclopentenyl cytosine, (CPE-C, NSC375575) which is a pyrimidine analogue of the fermentation-derived purine carbocyclic nucleoside, neplanocin A, has demonstrated significant antitumor activity against the ara-C resistant lines of P388 and L1210 leukemia in vivo. Multiple long term survivors were produced in these tumor models. This compound also gives 100% growth inhibition of the solid human A549 lung and the MX-1 mammary tumor xenografts grown in immunocompromised (athymic) mice. Good activity was also observed against a third human tumor xenograft model, metastatic LOX melanoma.

CPE-C has significant activity against both DNA and RNA viruses in vitro. Potent activity is observed against HSV-1 (TK+ and TK−), HSV-2, vaccinia, cytomegalovirus, and varicella-zoster virus. Good activity was also found against a strain of influenza virus (Hong Kong flu), vesicular stomatitis virus, Japanese encephalitis virus, and Ponto Toro virus. Excellent activity was found against the vaccinia virus in vivo using the mouse tail pox model.

BRIEF DESCRIPTION OF THE DRAWING

The sole figure shows the reaction scheme for preparing CPE-C. Route A shows the direct displacement method while Route B describes the alternative aglycon ring building approach to CPE-C.

DETAILED DESCRIPTION OF THE INVENTION

Figure 1:
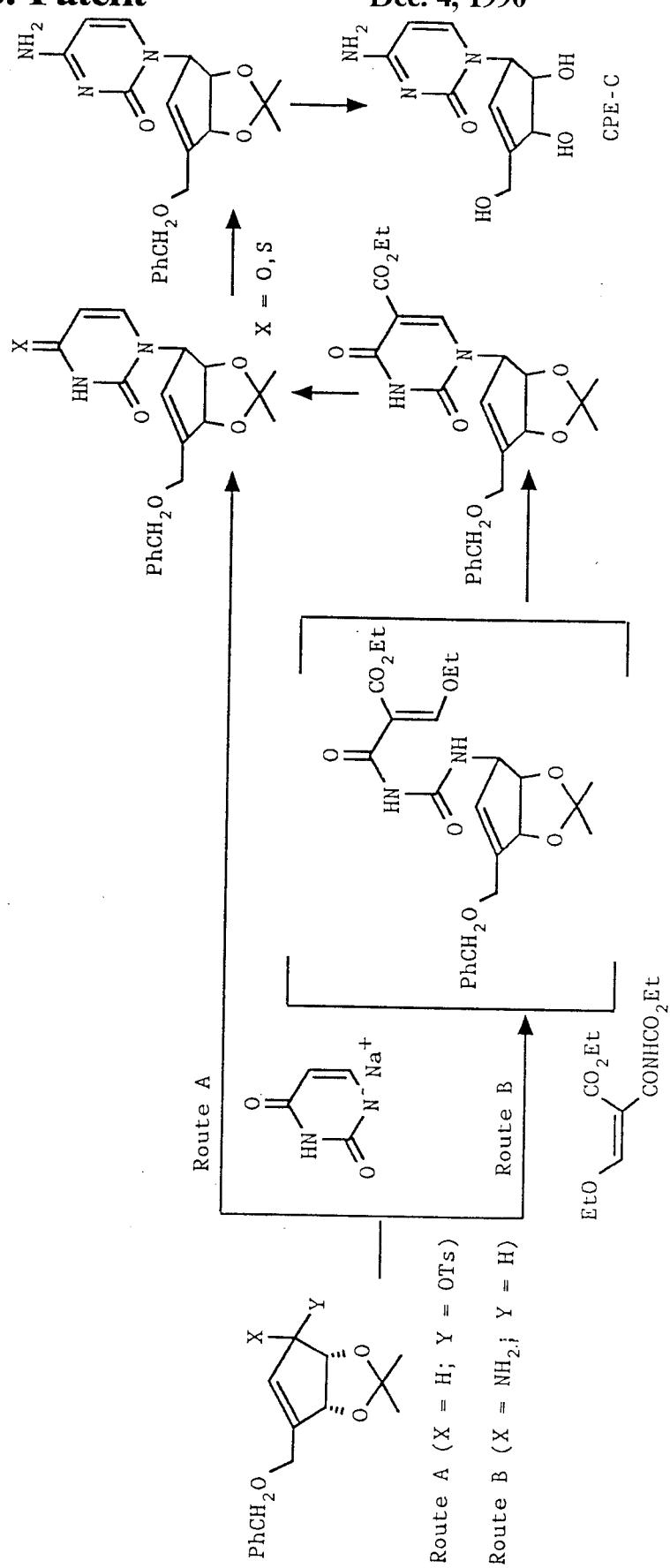

The activity of CPE-C against both DNA and RNA viruses is surprising in view of the unpredictability of activity among standard furanosyl nucleosides and the unconventional carbocyclic cyclopentenyl nucleosides. For example, the conventional 2′, 3′-dideoxyribofuranosyl nucleosides are very active against the AIDS virus [Mitsuya and Broder, *PNAS, U.S.A.* 83, 1911 (1986)] while the corresponding 2′,3′-dideoxycyclopentenyl nucleosides have no activity against the AIDS virus [Marquez et al., *Nucleosides and Nucleotides*, 6,239 (1987)]. The unpredictability in the extrapolation of biological results is further illustrated in the anticancer drug field by the well-known activity of arabinofuranosyl cytosine (ara-C) against human and animal tumors, the activity of the carbocyclic, cyclopentanyl (saturated) analogue with arabinosyl stereochemistry against L1210 leukemia [Shealy and O'Dell, *J. Pharm. Chem.*, 68, 668 (1979)] and the complete lack of antitumor activity of the cyclopentenyl (unsaturated) analogue of CPE-C with arabinosyl stereochemistry.

Compounds Described

Using prior art (Lim and Marquez), *Tetrahedron Letters*, 1983, 24: 5559-62, the stereoselective synthesis of alcohol (Formula 1) was performed. This compound was functionalized to have a reactive leaving group, such as a tosylate, which constitutes a key step in the simplified methodology to generate cyclopentenyl carbocyclic nucleosides by a direct-displacement reaction (Examples B, E, F, Q and R). The protected compounds obtained from this procedure can then be further manipulated and their protective groups removed to give biologically active compounds such as neplanocin A (Examples C and D), 3-deazaneplanocin A (Examples G and H), 2′,3′-dideoxycyclopentenyl cytosine (Examples I through P), etc. These latter transformations are virtually unlimited by the use of conventional organic chemistry and involve the removal, substitution and inversion of the hydroxyl groups at positions 2′ and 3′ of the cyclopentenyl ring. Through these procedures the corresponding 2′-deoxy-, 3′-deoxy-, ara-, xylo-, lyxo- , and dideoxy analogues of purine, pyrimidine or other heterocyclic cyclopentenyl nucleosides can be obtained.

An important part in the use of the direct-displacement reaction to obtain these compounds is the determination of the exact site of attachment of the cyclopentenyl moiety to the heterocyclic bases. This has been accomplished by the use of $^{13}$C-NMR spectroscopy or $^1$H-NMR Nuclear Overhauser Enhancement (NOE) measurements. The NOE experiments leading to the correct assignment of the structure of 3-deazaneplanocin A as the N-9 isomer are given in Example S using the precursor chloro compound obtained in Example G.

It has been found that cyclopentenyl carbocyclic nucleosides can be prepared according to the displacement reaction of the present invention. The reaction is as follows, as shown in Equation I.

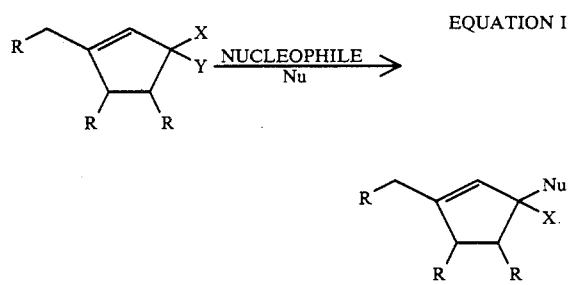

EQUATION I wherein X and Y are selected from the group consisting of H, $OSO_2C_6H_4CH_3$, $OSO_2CH_3$, $OSO_2CF_3$, F, Cl, Br, I, $OCOCH_3$, and $OCOC_6H_5$, OH, with the premise that X and Y cannot both be H.

R is selected from the group H, OH, O-acyl, O-aryl and O-silyl.

The nucleophilic bases for use in this reaction are selected from the group consisting of purines, pyrimidines, and five and six membered aglycons. The heterocyclic nucleophiles may be present as a salt or as a free base. The nucleophile may also be a simple nucleophile as such as NaCN, $NaN_3$, or CH≡CNa.

The displacement reaction results in a Walden inversion at the electrophilic carbon atom. Equation I illustrates the case where X=H and Y=leaving group as defined above.

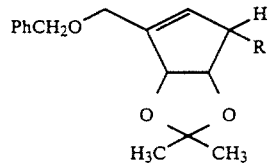
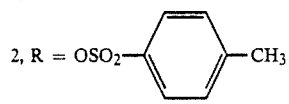
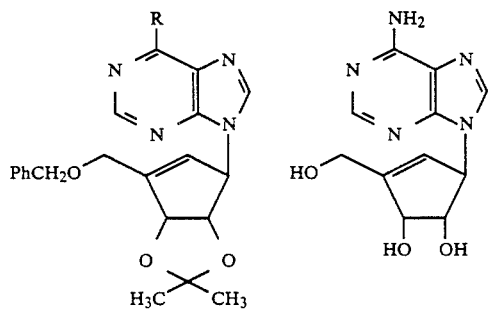
FORMULA 1, R = OH
2, R = OSO₂—C₆H₄—CH₃
3, R = Cl
4, R = NH₂
5
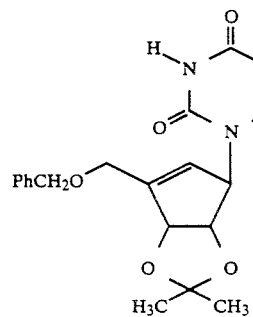
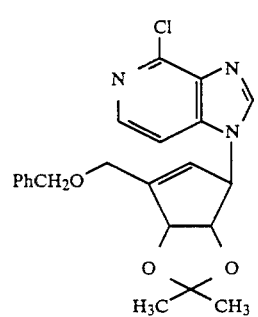
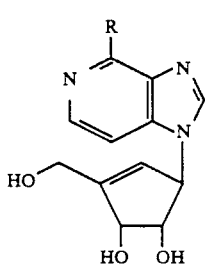
6
7
8, R = Cl
9, R = NH₂
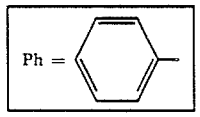
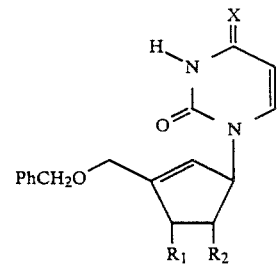
10, $R_1 = R_2 = OH$; $X = O$
11, $R_1 + R_2 = O-C(=S)-O$; $X = O$
12a, $R_1 = H$; $R_2 = OH$; $X = O$
12b, $R_1 = OH$; $R_2 = H$; $X = O$
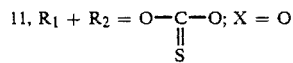
13, $R_1 = O-C(=S)-N(\text{imidazolyl})$; $R_2 = H$; $X = O$
14, $R_1 = R_2 = H$; $X = O$
15, $R_1 = R_2 = H$; $X = S$ -continued

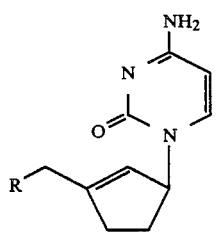
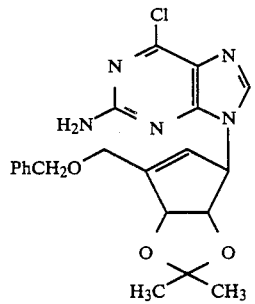
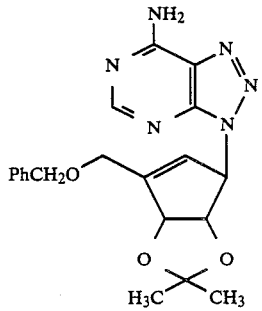

16, R = OCH₂Ph
17, R = OH

18

19

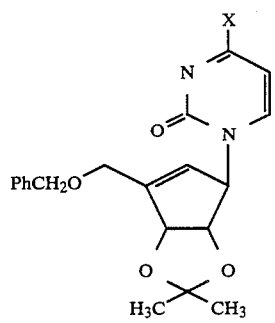
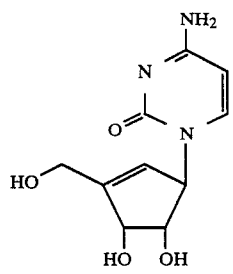
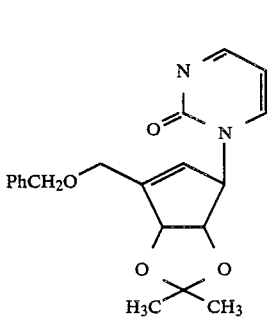
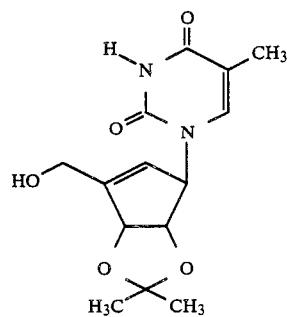

20, X = SH
21, X = NH₂

22

23

24

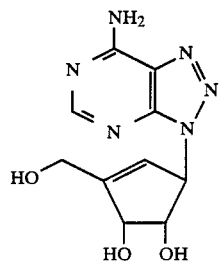
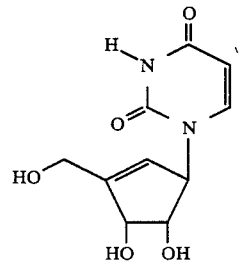
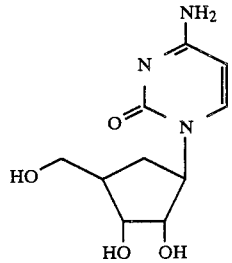
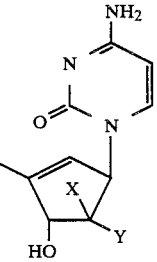

25

26

27

28, X = F; Y = H
29, X = H; Y = F

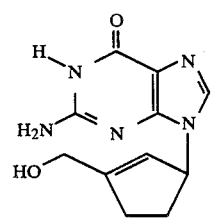
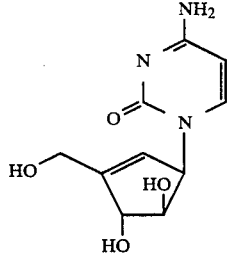
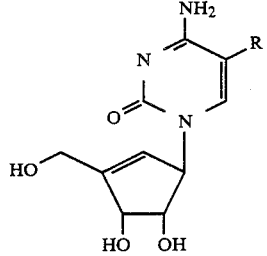

30

31

32, R = F
33, R = Cl
34, R = Br
35, R = I

The advantage of the displacement reaction for synthesizing these types of carbocyclic nucleosides is that previous methods of synthesizing these compounds required more synthetic steps (FIG. 1, Route B). For example, to prepare CPE-C, starting with the readily available D(+)-ribonic acid gamma-lactone, 2-cyclopentene-1-one was stereoselectively reduced to the corresponding allylic alcohol possessing the alpha configuration. This compound, in turn, was converted to the versatile 2-cyclopentenylamine after a three-step sequence which included tosylation, SN₂ displacement with sodium azide, and reduction. The carbocyclic amine obtained then required four additional steps to complete the pyrimidine ring of CPE-C.

The displacement reaction sequence (FIG. 1, Route A) applied to the synthesis of CPE-C (Formula 22) is described in Example E.

The new displacement method of synthesizing carbocyclic nucleosides greatly simplifies the preparation of these compounds.

Stereoselective reduction of the cyclopentenyl double bond can be accomplished to produce the corresponding saturated carbocyclic compounds (aristeromycin analogs).

EXAMPLE A (1S,2S,3R)-4-Benzyloxymethyl-2,3-O-(methylethylidine)-4-cyclopentene-1-olp-toluene-sulfonate ester (Formula 2)

A solution of alcohol 1 (0.7068 g, 2.56 mmol), triethylamine (1.05 g, 10.4 mmol), and p-toluenesulfonyl chloride (1 g, 5.25 mmol) in 10 ml of dry methylene chloride was stirred overnight at room temperature. The reaction mixture was diluted with 100 ml of methylene chloride, washed with water, dried (MgSO$_4$), and concentrated in vacuo. Flash column chromatography, using hexane-ethyl acetate (3:2) afforded 0.9 g (82%) of 2 as a white solid, mp 65–68.C.; $^1$H—NMR (CDCl$_3$) δ2.27 and 2.29 (singlets, 6H, isopropyl), 2.40 (s, 3H, PhCH$_3$) 4.10 (d, J=2 Hz, 2H, H-6$_{a,b}$), 4.48 (s, 2H, OCH$_2$Ph), 4.67 (dd, J=4 Hz, 1H, H-2), 4.82 (d, J=4 Hz, 1H, H-3), 5.18 (m, 1H, H-1), 5.63 (br s, 1H, H-5), 7.24 (s, 5H, Ph), 7.25 (d, J=8 Hz, 2H, aromatic), 7.80 (d, J=8 Hz, b 2H, aromatic).

EXAMPLE B

6-Chloro-9-[(1'R,2'S,3'R)-4'-benzyloxymethyl-2'3'O (methylethylidene-4'-cyclopenten-1'-yl]-9H-purine (Formula 3)

6-Chloropurine (0.4 g, 2.59 mmol) was added to a stirred suspension of NaH (82 mg as an 80% oil suspension) in 10 ml of dry acetonitrile at room temperature, and stirring was continued for 40 min. The tosylate 2 (0.32 g, 0.743 mmol) was added and the resulting mixture was refluxed for 3 h. After allowing the reaction to cool to room temperature, the mixture was diluted with 100 ml of methylene chloride, filtered, and the filtrate was concentrated in vacuo. Column chromatography on silica gel, eluting with hexane-ethyl acetate (1:1), afforded 95 mg (31%) of 3: $^1$H-NMR (CDCl$_3$) δ 1.35 and 1.48 (singlets, 6H, isopropyl), 4.29 (s, 2H, H-6'$_{a,b}$), 4.62 (s, 2H, OCH$_2$Ph), 4.73 (d, J=5.5 Hz, 1H, H-2'), 5.40 (d, J=5.5 Hz, 1H, H-3'), 5.64 (s, 1H, H-1'), 5.83 (d, J=1 Hz, 1H, H-5'), 7.34 (m, 5H, Ph), 8.01 (s, 1H, H-2), 8.75 (s, 1H, H-8).

EXAMPLE C

9-[(1'R,2'S,3'R)-4-Benzyloxymethyl-2',3'-O-(methylethylidene)-4-cyclopenten-1'-yl] adenine (Formula 4)

Method A

A solution of the protected nucleoside 3 (50 mg, 0.12 mmol) was heated in a steel bomb at 70° C. for 5 days in saturated (at 0° C.) methanolic ammonia (100 ml). After the excess ammonia was allowed to escape, the reaction mixture was concentrated in vacuo. Column chromatography on silica gel, eluting with ethyl acetate, afforded 35.6 mg (75%) of 4; $^1$H-NMR (CDCl$_3$) δ 1.36 and 1.48 (singlets, 6H, isopropyl), 4.29 (s, 2H, H-6'$_{a,b}$), 4.63 (s, 2H, OCH$_2$Ph), 4.72 (d, J=5.6 Hz, 1H H-3'), 5.38 (d, J=5.5 Hz, 1H, H-2'), 5.57 (d, J=1.5 Hz, 1H, H-1'), 5.70 (s, 2H, NH$_2$), 5.82 (m, 1H, H-5') 7.35 (m, 5H, Ph), 7.67 (s, 1H, H-2), 8.36 (s, 1H, H-8)

Method B

Adenine (0.1265 g, 0.936 mmol) was added to a stirred suspension of NaH (30 mg as an 80% oil suspension) in 5 ml of dry acetonitrile at room temperature, and stirring was continued for 40 min. The tosylate 2 (0.2687 g, 0.625 mmol) was added and the resulting mixture was stirred at 70° C. for 24 h. After allowing the reaction mixture to cool to room temperature, the mixture was diluted with 50 ml of methylene chloride, filtered and the solvent was concentrated in vacuo. Column chromatography on silica gel, eluting with ethyl acetate and 10% methanol in ethyl acetate, gave 32 mg (8.6%) of 4.

EXAMPLE D

9[(1'R,2'S,3'R)-4'-Hydroxymethyl-2',3'dihydroxy-4 cyclopenten-1'-yl]adenine (Formula 5). Neplanocin A Boron trichloride (1.3 ml of a 1M solution in methylene chloride, 1.3 mmol) was added to a solution of the protected Neplanocin A(4) (0.108 g, 0.274 mmol) in dry methylene chloride (8 ml) at −78° C. The reaction mixture was stirred for an additional 3 h at −78° C. followed by the addition of 60 ml of methanol. The solvent was removed in vacuo and another 60 ml of methanol was added to the residue. The solvent was again removed in vacuo. The residue was partitioned between water and ethyl acetate and the aqueous layer was lyophilized to afford a solid. Chromatography on a C-18 reversed-phase Sep-Pak ® cartridge, eluting with water, gave 45.5 mg (63%) of 5 which was recrystalized from methanol; mp 222-225 C; $^1$H—NMR (D$_2$O) δ 4.16 (s, 2H, H-6'$_{a,b}$), 4.35 (dd, J=5.5 Hz, H-2'), 4.49 (d, J=5.5 Hz, H-3'), 5.47 (m, 1H, H-1'), 5.75 (d, J=1.5 Hz, 1H, H-5'), 8.27 (s, 1H, H-8), 8.35 (s, 1H, H-2).

EXAMPLE E

1-[(1'R,2'S,3'R) 4'-Benzyloxymethyl-2',3'-O-(methylethylidene)-4'-cyclopenten-1'-yl]-2.4 (1H,3H)pyrimidinedione (Formula 6)

A mixture of uracil (80 mg, 0.714 mmol), the tosylate 2 (100 mg, 0.232 mmol) and anhydrous potassium carbonate (108 mg) was stirred in anhydrous DMSO (2 ml) at room temperature for 36 h. Water was added and the mixture was extracted with chloroform. The organic layer was dried and concentrated to give an oily residue. Chromatography on preparative TLC silica gel plates, eluting with ethyl acetate, gave 22.5 mg (26%) of 6. $^1$H—NMR (CDCl$_3$) δ 1.35 and 1.43 (singlets, 6H, isopropyl), 4.23 (s, 2H, H-6'$_{a,b}$), 4.60 (m, 3H, H-2'and OCH$_2$PH), 5.20 (d, J=5.2 Hz, 1H, 3'), 5.39 (S, 1H, H-1')5.66 (m, 2H, H-5and H-5'), 7.00 (d, J=8 Hz, 1H, H-6), 7.35 (s, 5H, Ph).

EXAMPLE F

4-Chloro-1-[1'R,2'S,3'R)-4'-benzyloxymethyl-2',3'-O-(methylethylidene)-4'-cyclopenten-1'-yl]imidazo[4,5-c]pyridine (Formula 7)

6-Chloro-3-deazapurine (30 mg. 0.195 mmol) was added to a suspension of NaH (7.5 mg as an 80% oil suspension) in anhydrous acetonitrile (2 ml) at room temperature. The resulting mixture was stirred at room temperature for 40 min before the tosylate 2 (0.126 g, 0.29 mmol) was added). After refluxing for 5 h, the mixture was cooled, diluted with methylene chloride, and the insoluble material was removed by filtration. The filtrate was concentrated to yield 47.4 mg (59%) of crude product as a mixture of N-7 and N-9 substituted isomers, from which 26.2 mg (33%) of the desired and less polar N-9 isomer was obtained after chromatography on a silica gel column (ethyl acetate-hexane, 1:1) as a foam; $^1$H-NMR (CDCl$_3$) δ 1.34 and 1.49 (singlets, 6H, isopropyl), 4.30 (s, 2H, H-6'$_{a,b}$), 4.56 (d, J=5.8 Hz, 1H, H-2'), 4.66 (s, 2H, OCH$_2$Ph), 5.28 (d, J=5.8 Hz, 1H, H-3'), 5.39 (br s, 1H, H-1'), 5.96 (br s, 1H, H-5'), 7.40 (d, J=5.4 Hz, 1H, H-3), 7.42 (m, 5H, Ph), 7.90 (s, 1H, H-8), 8.23 (d, J=5.4 Hz, 1H, H-2).

EXAMPLE G

4-Chloro-1-[(1'R,2'S,3'R) 4'-hydroxymethyl 2', 3'-dihydroxy-4'-cyclopenten-1-yl]imidazo[45-c]pyridine (Formula 8)

Boron trichloride (0.5 ml of a 1M solution in methylene chloride, 0.5 mmol) was added to a solution of the protected compound ∂(20 mg, 0.05 mmol) in dry methylene chloride (1 ml) at −78° C. for 3 h. Methanol (10 ml) was added and the mixture was concentrated to dryness. Another portion of methanol was added and again evaporated. The residue was partitioned between water and ethyl acetate. The aqueous layer was lyophilized to afford a solid (11.3 g, 82%). Flash chromatography on a C18 column, eluting with 20% methanol in water, gave the purified product as a white solid after lyophilization, mp 219°-220° C.; $^1$H-NMR (DMSO$_6$) δ 4.03 (dd, J=5.6 Hz, 1H, H-2'), 4.14 (s, 2H, H-6'$_{a,b}$), 4.38 (d, J=5.6 Hz, 1H, H-3'), 5.40 (m, 1H, H-1'), 5.83 (br s, 1H, H-5'), 7.63 (d, J=5.8 Hz, 1H, H-3), 8.11 (d, J=5.8 Hz, 1H, H-2), 8.36 (s, 1H, H-8).

EXAMPLE H

4 Amino-1-[1'R,2'S,3'R)-4'-hydroxymethyl-2', 3'-dihydroxy-4'-cyclopenten-1'-yl]imidazo [4,5-c]pyridine (Formula 9). 3-Deazaneplanocin A.

The cyclopentenyl 6-chloro-3-deazapurine 8 (11 mg, 0.039 mmol) was heated with anhydrous hydrazine (0.5 ml) at 100 C for 1 h. The solution was concentrated in vacuo to give a glassy residue. To this residue degased water was added (1 ml) followed by Raney nickel (100 mg), and the resulting mixture was refluxed for 1 h. The catalyst was filtered off and the filtrate was subjected to C$_{18}$ a reversed-phase flash column chromatography, eluting with 20% methanol in water to give 7 mg (70%) f 3-deazaneplanocin as a lyophilized powder; $^1$H-NMR (D$_2$O) δ 4.35 (m, 1H, H-2'), 4.41 (s, 2H, H-6'$_{a,b}$), 4.69 (d, J=5.6 Hz, 1H, H-3'), 5.53 (m, 1H, H-1'), 6.09 (br s, 1H, H-5'), 7.21 (d, J=7.4 Hz, 1H, H-3), 7.65 (d, J=7.4 Hz, 1H, H-2), 8.31 (s, 1H, H-8). The UV spectrum of 3-deazaneplanocin ( max 262, pH 7) was, as expected, superimposable on that of 3-deazaaristeromycin. MS (FAB, positive mode), m/z (rel. intensity) 2673 (MH+, 36.7), 135 (b+2H, 21.6); High resolution FAB MS, m/z 263.112 (MH+, calcd. 263.224); [α]D$^{24}$ −13.5° (c 0.112, H$_2$O).

EXAMPLE I

1[(1'R,2'S,3 R)-4'-Benzyloxymethyl-2', 3'-dihydroxy-4'-cyclopenten-1'-cyclopenten-1'-yl]-2,4(1H,3H)-pyrimidinedione (Formula 10)

To a stirred solution of 6 (1.5 g, 4 mmol) in methanol (75 ml) was added cation exchange resin (24 g, 30 equiv., Bio-Rad AG 40W-X8), pre-washed in methanol. The mixture was stirred at 50. for 16 h, followed by filtration, concentration of the methanolic solution, and purification via flash column chromatography (BioRad Bio-Sil A, 200–400 mesh), eluting first with 15:1 CH$_2$Cl$_2$:MeOH and then 10:1 g CH$_2$Cl$_2$:MeOH to give 10 as a white foam (1.25 g, 95%); $^1$H-NMR (Acetone-d$_6$) δ 4.22 (m, 3H, H-6'$_{a,b}$ and H-2'), 4.60 (m,3H, OCH$_2$Ph and H-3'), 5.45 (br s, 1H, H-1'), 5.58 (d, J−6 Hz, 1H, H-5), 5.78 (d, J<1 Hz, 1H, H-5'), 7.34 (d, J=6 Hz, 1H, H-6), 7.36 (m, 5H, Ph).

EXAMPLE J

1-[(1'R,2'S,3'R)-4'-Benzyloxymethyl-2',3'-O-thiocarbonate-4'cyclopenten-1'-yl]-2,4(1H, 3H)-pyrimidinedione (Formula 11)

To a stirred solution of 10 (1.03 g, 3.1 mmol) in dry DMF (25 ml) was added thiocarbonyldiimidazole (0.837 g, 1.5 equiv). The resulting yellow solution was stirred at room temperature for 40 h under nitrogen, followed by concentration under reduced pressure. The residue was taken up in dichloromethane and chromatographed (Kieselgel 60, 70-230 mesh) via gravity column chromatography, eluting with 10:1 CH$_2$Cl$_2$:MeOH. Recrystallization from dichloromethane afforded 1.0 g (87%) of 3, as a white crystalline material, mp >130 C; $^1$H-NMR (Acetone-d$_6$) δ 4.32 (m, 2H, H-6'$_{a,b}$), 4.62 (dd, J=20 Hz, J'=14 Hz, 2H, OCH$_2$Ph), 5.46 (s, 1H, H-1'), 5.62 (d, J=6 Hz, 1H, H-5), 5.77 (d, J=4 Hz, 1H, H-2'), 6.14 (s, 1H, H-5'), 6.16 (d, J=4 Hz, 1H, H-3'), 7.40 (m, 5H, Ph), 7.58 (d, J=6 Hz, 1H, H-6).

EXAMPLE K

1-[1R,2'S) 4'-Benzyloxymethyl-2'-hydroxy-4'-cyclopenten-1'-yl]-2,4-(1H,3H)pyrimidinedione and 1-(1'R,3'R)-4'-Benzyloxymethyl-3'-hydroxy-4'-chclopenten-1'-yl]-2,4(1H, 3H) pyrimidinedione Formulas 1a,b)

To a stirred solution of 11 (0.993 g, 2.66 mmol) in dry toluene (30 ml) were added azoisobutyronitrile (0.765 g, 1.75 equiv) and tributyltin hydride (2.2 ml, 3 equiv). The resultant solution was refluxed for 1 hr, cooled, concentrated under reduced pressure, and the residue was dissolved in dichloromethane for purification on a gravity column (Kieselgel-60, 70-230 mesh), eluting with 10:1 CH$_2$Cl$_2$:MeOH to give 835 mg (100%) Of 12a and 12b as foams. TLC in 10:1 CH$_2$Cl$_2$:MeOH distinctly revealed the presence of both monohydroxyl compounds.

Compound 12a—$^1$H-NMR (CDCl$_3$) δ 2.48 (dd, J=16 Hz, J'=Hz, 1H, H-2'β), 2.96 (dd, J=16 Hz, J'=7 Hz, 1H, H-2'α), 4.09 (s, 2H, H-6'$_{a,b}$), 4.56 (s, 2H, OCH$_2$Ph), 4.92 (m, 2H, H-1'and H-3'), 5.69 (d, J=6 Hz, 1H, H-5), 5.79 (s, 1 H, H-5'), 7.12 (d, J=6 Hz, 1H, H-6), 7.35 (s, 5H, Ph), 9.20 (s, 1H, NH).

Compound 12b-$^1$H-NMR (CDC13) δ 2.40 (br d, J=18 Hz, 1H, H-3'α), 2.83 (dd, J=17 Hz, J'=8 Hz, 1H, H-3 β), 4.10 (s, 2H, H-6'$_{a,b}$), 4.40 (m, 1H, H-2'), 4.57 (s, 2H, OCH$_2$Ph), 5.38 (s, 1H, H-1'), 5.52 (s, 1H, H-5'), 5.64 (d, J=6 Hz, 1H, H-5), 7.15 (d, J=6 Hz, 1H, H-6), 7.35 (s, 5H, Ph), 9.78 (br, s, 1H, NH).

EXAMPLE L

1[(1'R,3'R)-4'-Benzyloxymethyl-3'-O-(1-imidazolyl)thiocarbonyl-4'-cyclopenten-1'-yl]-2,4(1H,3H)pyrimidinedione (Formula 13)

To a stirred solution of 12a and 12b (0.817 g, 2.5 mmol) in dry DMF (25 ml) was added thiocarbonyldiimidazole (0.695 g, 1.5 equiv). The resulting yellow solution was stirred at room temperature for 40 hr under nitrogen, whereupon TLC (10:1 $CH_2Cl_2$:MeOH) revealed total disappearance of starting materials, the presence of the less polar product, and also the presence of an unexpected polar compound. Removal of DMF was followed by flash column chromatography (eluant, ethyl acetate) to give 658 mg (60%) of specifically one monothiocarbonylimidazole species (13). NMR analysis of the polar component, via selective proton irradiation studies, enabled the definite assignment of that material as the 2,2'-anhydronucleoside, arising from the 3'-deoxy starting material. Compound 13 was obtained as a foam; $^1$H-NMR (CDC13) δ 2.60 (d, J=12 Hz, 1H, H-2'β), 3.27 (dd, J=16 Hz, J'=8 Hz, 1H, H-2'α), 4.14 (s, 2H, H-6'$_{a,b}$), 4.60 (s, 2H, OCH$_2$Ph), 5.63 (br s, 1H, H-1'), 5.76 (m, 2H, H-5 and H-3'), 5.90 (br s, 1H, H-5'), 7.04, 7.63, 8.02 (singlets, 3H imidazole), 7.13 (d, J=6 Hz, 1H, H-6), 7.36 (s, 5H, Ph), 8.36 (s, 1H, N-H).

EXAMPLE M

1-[(1'R)-4'-Benzyloxymethyl-4'-cyclopenten-1'-yl]-2,4(1H,3H)pyrimidinedione (Formula 14)

To a stirred solution of 13 (0.611 g, 1.44 mmol) in dry toluene (20 ml) were added azoisobutyronitrile (0.415 g. 175 equiv) and tributyltin hydride (1.2 ml, 3 equiv). The resultant solution was refluxed for 1 hr, cooled and concentrated under reduced pressure; the residue was taken up in ethyl acetate and purified by gravity column chromatography (eluant, ethyl acetate) to give 6 (287 mg, 67%) of 14 as a foam; $^1$H-NMR (CDCl$_3$) δ 1.70 (m, 1H, H-2'α) 2.52 (m, 3H, H-3'α, 3'β, 2'β), 4.12 (s, 2H, H-6'$_{a,b}$), 4.56 (s, 2H, OCH$_2$PH), 5.56 (m, 1H, H-1'), 5.67 (d, J=6 Hz, 1H, H-5 and m, 1H, H-5'), 7.12 (d, J=6 Hz, 1H, H-6), 7.34 (s, 5H, Ph), 9.18 (br s, 1H, N-H).

EXAMPLE N

1-[(1'R)-4'-Benzyloxymethyl 4-cyclopenten-1'-yl]-4-thio-2(1H,3H)pyrimidinone (Formula 15)

To a solution of 14 (0.287 g, 0.96 mmol) in dry benzene (20 ml) was added with stirring 2.4-bis(4-methoxyphenyl)-1,3-dithia-2,4-diphosphetane-2,4disulfide (Lawesson reagent) (0.505 g, 1.3 equiv). The mixture was refluxed between 0.75–1 hr under Argon, whereupon TLC in 3:7 ethyl acetate:petroleum ether revealed total consumption of starting material. Removal of benzene under reduced pressure, followed by flash column chromatography (eluting first with 1:5 ethyl acetate:petroleum ether and then 1:3 of the same solvent mixture) gave 16yO mg (53%) of 15 as a yellow foam; $^1$H-NMR (CDCl$_3$) δ 1.72 (m, 1H, H-2'α), 2.54 (m, 3H, H-3'α, 3'β, 2'β), 4.14 (s, 2H, H-6'$_{a,b}$), 4.58 (s, 2H, OCH$_2$Ph), 5.58 (m, 1H, H-5'), 5.64 (m, 1H, H-1'), 6.37 (dd, J=6 Hz, J'<1Hz, 1H, H-5), 6.98 (d, J=6 Hz, 1H, H-6), 7.36 (s, 5H, Ph), 9.71 (br s, 1H, N-H).

EXAMPLE O

4-Amino-1-[1'R)-4'-Benzyloxymethyl-4'cyclopenten-1'-1'-yl]-2(1H)pyrimidinone (Formula 16)

The thiouracil analog 15 (0.095) g, 0.3 mmol) was heated in methanolic ammonia (25 ml) in a sealed pressure bottle at 80 for 20 h. TLC in 10:1 $CH_2Cl_2$:MeOH revealed nearly complete conversion to 16. Evaporation of ammonia and concentration of the crude material was followed by purification via prep TLC (2000 μ) in 10:1 $CH_2Cl_2$:MeOH to give 19 mg of recovered starting material and 45 mg (62%) of 16 obtained as a foam; H-NMR (CDCl$_3$) δ 1.66 (m, 1H, H-2'α) 2.54 (m, 3H, H-3'α, 3'β, 2'β) 4.14 (s, 2H, H-6'$_{a,b}$), 4.56 (s, 2H, OCH$_2$Ph), 5.60 (s, 1H, H-1'), 5.75 (d, J=5 Hz, 1H, H-5 and m, 1H, H-5'), 7.25 (d, J=5 Hz, 1H, H-6), 7.34 (s, 5H, Ph).

EXAMPLE P

4-Amino-1-[(1'R)-4'-hydroxymethyl-4'-cyclopenten-1'-yl]-2(1H)pyrimidinone (Formula 17)

To a solution of 16 (0.036 g, 0.12 mmol) in dry dichloromethane (1.5 ml), chilled to −78°, was added fresh boron trichloride (1M in dichloromethane, 3 equiv). The mixture was stirred for 1 h at −78° whereupon TLC (10:1 $CH_2Cl_2$:MeOH) revealed the completion of the reaction. Excess boron trichloride was quenched by the addition of methanol (5 ml×3) followed by evaporation (×3). The cream colored crude foam was purified via reversed phase column chromatography, eluting with 20% methanol to obtain the desired 2', 3'-dideoxycyclopentenyl cytosine 17 in 70% yield; $^1$H-NMR (D$_2$O) δ 1.69 (m, 1H, H-2'α) 2.42 (m, 3H, H-3'α, 3'β, 2'β), 4.21 (s, 2H, H-6'$_{a,b}$), 5.51 (br s, 2H, H-1'and H-5'), 5.91 (d, J=6 Hz, 1H, H-5), 7.45 (d, J=6 Hz, 1H, H-6).

EXAMPLE O

2-Amino-6-chloro-9-(1'R,2'S,3'R) 4'-benzyl-oxymethyl-2', 3'-O-(methylethylidene) 4'-cyclopenten-1'-yl]-9H-purine (Formula 18)

A mixture of the cyclopentenyl tosylate 2 (0.25 g, 0.58 mmol), 2-amino-6-chloropurine (0.212 g, 1.25 mmol, 2.2 eq), and K$_2$CO$_3$ (1 g) was suspended in 2 mL of DMSO and stirred at room temperature for 42 h. The suspension was then poured into CH$_2$Cl$_2$and washed with dilute NaCl. Evaporation of the CH$_2$Cl$_2$gave an oil which was further dried under high vacuum to remove residual DMSO. Purification by preparative TLC (silica, 3:2 EtOAc:Hexane) gave two major purine containing products of which the faster moving and predominant was the desired N-9 alkylated purine 18 (0.117 g, 47%), mp 137°–140°; $^1$H-NMR (CDCl$_3$) δ 1.35 (s, 3H, CH$_3$), 1.46 (s, 3H, CH$_3$), 4.27 (s, 2H, H-6'$_{a,b}$), 4.61 and 4.62 (2H, PhCH$_2$), 4.67 (d, J=5.3 Hz, 1H, H-2'), 5.10 (br s, 2H, NH$_2$, exchangeable), 5.36 (d, J=5.3 Hz, 1H, H-3'), 5.43 (br s, 1H, H-1'), 5.78 (br s, 1H, H-5'), 7.34 (m, 5H, Ph), 7.65 (s, 1H, H-8); $^{13}$C-NMR (CDCl$_3$) δ 25.8 (CH$_3$), 27.2 (CH$_3$), 64.3 (C-1'), 66.2 (C-6'), 72.8 (PhCH$_2$), 83.7 (C-2'), 83.9 (C-3'), 112.4 (methylethylidene C), 122.7 (C-5'), 125.2 (d, J=12.6 Hz, C-5), 127.3 (Ph), 127.5 (Ph), 128.1 (Ph), 128.2 (Ph), 137.6 (Ph), 140.1 (dd, J=210 Hz, J'=4.4 Hz, C-8), 149.2 (C-4'), 151.0 (s, C-6), 153.2 (dd, J=4.7 Hz, J'=3.1 Hz, C-4), 159.1 (s, C-2).

The minor product was identified as the N-7 isomer: $^1$H NMR-(CDCl$_3$) δ 1.33 (s, 3H, CH$_3$), 1.44 (s, 3H, CH$_3$), 4.27 (s, 2H, H-6'$_{a,b}$), 4.60 (d, J=5.5 Hz, 1H, H-2'), 4.63 (s, 1H, PhCH$_2$), 5.21 (d, J=5.5 Hz 1H, H-3'), 5.36 (br s, 2H, NH$_2$, exchangeable), 5.84 (br s, 1H, H-1'), 5.91 (br, s, 1H, H-5'), 7.35 (m, 5H, Ph), 7.84 (s, 1H, H-8); 13C-NMR (CDCl$_3$/D$_2$O) δ 23.9 (CH$_3$), 27.4 (CH3), 66.5 (C-1'), 66.6 (C-6'), 73.3 (PhC*H$_2$), 83.4 (C-2'), 84.7 (C-3'), 112.7 (methylethylidene C), 116.3 (dd, J=4.9 Hz, J'=1.5 Hz, C-5), 121.9 (C-5'), 127.5 (Ph), 127.8 (Ph), 128.4 (Ph), 137.7 (Ph), 143.9 (s, C-6), 145.7 (dd, J=209 Hz, J'=4.5 Hz, C-8), 150.9 (C-4'), 159.6 (s, C-2), 164.4 (d, J=13.0 Hz, C-4).

EXAMPLE R

7-Amino-3-[1'R,2'S,3'R) 4'benzyloxymethyl-2',3'-O-(methylethylidene) 4'-cyclopenten-1'-yl]-3H-1,2,3-triazolo[4,5-d]pyrimidine (Formula 19)

The cyclopentenyl tosylate 2 (0.68 g, 1.58 mmol) and 8-azaadenine (0.62 g, 4.54 mmol, 2.9 eq) were combined in a small round bottomed flask, an excess of K$_2$CO$_3$ (2 g) was added, and the reaction mixture was suspended in 6 mL of DMSO. After the reaction mixture had stirred at room temperature for 20 h, the suspension was poured into CH$_2$Cl$_2$ and washed with dilute NaCl. Removal of the CH$_2$Cl$_2$ under vacuum was followed by high vacuum removal of residual DMSO. Purification on preparative TLC (silica, 3:2 EtOAc:Hexane) gave two base containing products of which the faster moving was the desired product (39 mg, 7%); 1H-NMR (CDCl$_3$/D$_2$O) δ 1.37 (s, 3H, CH$_3$), 1.49 (s, 3H, CH$_3$), 4.28 (s, 2H, H6'$_{a,b}$), 4.59 and 4.60 (2H, PhCH$_2$), 4.97 (d, J=5.6 Hz, 1H, H-2'), 5.49 (d, J=5.6 Hz, 1H, H-3'), 5.87 (br, s, 1H, H-1'), 5.97 (br s, 1H, H-5'), 6.69 (br, s, 2H, NH$_2$, exchangeable), 7.32 (m, 5H, Ph), 8.50 (s, 1H, H-2); $^{13}$C-NMR (CDCl$_3$/D$_2$O) δ 25.9 (CH$_3$), 27.5 (CH$_3$), 66.4 (C-6'), 67.8 (C-1'), 72.8 (PhC*H$_2$), 83.9 (C-2'), 84.5 (C3'), 112.6 (methylethylidene C), 123.7 (C-5'), 124.6 (s, C-5), 127.9 (Pph), 128.4 (Ph), 138.0 (Ph), 148.6 (C-4'), 148.9 (dd, J=10.2 Hz, J'=2.5 Hz, C-4), 155.8 (d, J=11.2 Hz, C-6), 156.5 (d, J=202.5 Hz, C-2).

EXAMPLE S

NOE experiments with 4-chloro-1-[(1'R,2'S,3'r)-4'hydroxymethyl-2',3'-dihydroxy-4 'cyclopenten-1'-yl]imidazo[4.5-c]pyridine (Formula 8)

Through space interactions between purine protons and cyclopentenyl protons were examined by irradiation (0.032 Watt) of the aglycon protons and integration of the signals corresponding to carbocyclic protons. An enhancement of 1.03 was considered to be experimentally significant. Irradiation at H-8 produced an enhancement of 1.11 of the anomeric (H-1') signal. Irradiation of H-2 enhanced only H-3 (1.10), while irradiation of H-3 enhanced H-2 (1.20), H-1'(1.10), and H-2 (1 03). These results are in agreement with the structure for the N-O isomer. As anticipated for the N-7 isomer, neither irradiation of H-2 nor H-3 produced any enhancement of the carboxylic proton signals.

EXAMPLE T 4-amino-(1'R,2'S,3'R)-4'-hydroxymethyl-4'cyclopenten-1'-yl]-2(1H)pyrimidinone (Formula 22) (CPE-C)

Employing the similar type of chemistry that permitted the conversion of compound formula 14 to compound formula 17 (Examples M through P), compound formula 6 was sequentially converted to the corresponding 4-thio compound (formula 20), the 4-amino compound (formula 21) and the final cyclopentenyl cytosine derivative (formula 22 after the removal of the blocking groups. The conversion of compound formula 6 to compound formula 20 proceeded in 58% yield; NMR (CDCl$_3$) δ 1.35 and 1.47 (singlets, 6H, isopropyl) 4.25 (s, 2H, H-6'$_{a,b}$), 4.62 (br s, 3H OCH$_2$Ph and H-2') 5.25 (d, J=5.5 Hz, 1H, H-3'), 5.30 (br s, 1H, H-1'), 5.60 (br s, 1H, H-5'), 6.38 (d, J=7.5 Hz, 1H, H-5), 6.81 (d, J=7.5 Hz, 1H, H-6), 7.37 (br s, 5H, Ph), 10.4 (br s, 1H, NH).

The conversion of formula 20 to compound formula 21 proceeded in 86% yield; NMR (CDCl$_3$) δ 1.38 and 1.45 (singlets, 6H, isopropyl), 4.25 (s, 2H, H-6'$_{a,b}$), 4.62 (br s, 3H, OCH$_2$Ph and H-3'), 5.20 (s, 1H, H-1'), 5.25 (d, J=5.5 Hz, 1H, H-3'), 5.62 (s, 1H, H-5'), 5.80 (d, J=7.5 Hz, 1H, H-5), 7.13 (d, J=7.5 Hz, 1H, H-6), 7.20 [br s, 5H, Ph).

The conversion of compound formula 21 to formula 22 proceeded in 73% yield to give a white solid, mp 138°-141° C.; [α]$_D^{25}$-104.5° (C0.13, H$_2$O); NMR (D$_2$O) δ 4.12 (t, J=6 Hz, $_1$H, H-2'), 4.30 (s, 2H, H-6'$_{a,b}$), 4.60 (d, J=6 Hz, 1H, H-3'), 5.45 (br s, 1H, H-1'), 5.81 (d, J<1 Hz, 1H, H-5'), 6.00 (d, J=7.3 Hz, 1H, H-5), 7.22 (d, J=7.3 Hz, 1H, H-6), MS (FAB, positive mode), M/Z 240 (MH+). Analysis: Calc. C$_{10}$H$_{13}$N$_3$O$_4$, C, 50.21%; H, 5.48%, N, 17.51%. Found C, 50.17%; H, 5.39%; N, 17.49%.

EXAMPLE U

1-[(1'R,2'S,3'R)-4'-Benzyloxymethyl-2',3'-O-(methylethylidene)-4'-cyclopenten-1'-yl]-2(1H)pyrimidinone (Formula 23)

A solution of alcohol 1 (236) mg, 0.85 mmol), triphenyl phosphine (224 mg. 0.85 mmol), and diethyl azodicarboxylate (148.7 mg, 0.85 mmol) in dry DMF (5 ml) was reacted with 2(1H)pyrimidinone (70 mg, 0.85 mmol) dissolved in 1 ml of dry DMF and the resulting mixture stirred at room temperature for two days. After removing the solvent in vacuo, the residue was prepurified by passing it through a short silica gel column eluted first with benzene and then with CH$_2$Cl$_2$ in order to remove a polar impurity. The collected material was then purified by reverse phase HPLC chromatography on a C-18 column using 10% aqueous methanol to afford 63 mg (22%) of pure 23 as a foam; NMR (CDCl$_3$) δ 1.38 and 1.44 (singlets, 6H, isopropylidene, 4.20 (s, 2H, H-6'$_{a,b}$), 4.60 (s, 2H, OCH$_2$Ph), 4.80 (d, J=6 Hz, 1H, H-3'), 5.25 (d, J=6 Hz, 1H, H-2') 5.85 (s, 1H, H-1'), 6.00 (s, 1H, H-5'), 6.95 (t, J=4.8 Hz, 1H, H-5), 7.30 (br s, 5H, Ph), 8.52 (d, J=4.8 Hz, 2H, H-4 and H-6).

EXAMPLE V

5 Methyl-1-[(1'R,2'S3'R)-4'-benzyloxymethyl-2', 3'-O-(methylethylidene)-4'-cyclopenten-1'-yl]- 2,4(1H,3H)pyrimidinedione (Formula 24)

A mixture of thymine (45 mg, 0.35 mmol), the tosylate 2 (50 mg, 0.116 mmol) and anhydrous potassium carbonate (54 mg) was stirred in anhydrous DMSO (1 ml) at room temperature for 36 h. After this time, the mixture was diluted with water (50 ml) and extracted four times with CH$_2$Cl$_2$. The combined organic extracts were reduced to dryness and chromatographed on preparative TLC silica gel plates with ethyl acetate to give 6 mg (13.4%) of 24; $^1$H-NMR (CDCl$_3$) δ 1.34 and 1.44

(singlets, 6H, isopropyl), 1.88 (s, 3H, CH₃), 4.22 (s, 2H, H-6′$_{a,b}$), 4.56 (br s, 3H, OCH₂Ph and H-2′), 5.20 (d, J=6 Hz, 1H, H-3′), 5.38 (s, 1H, H-1′), 5.62 (s, 1H, H-5′), 6.78 (s, 1H, H-6), 7.34 (br s, 5H, Ph), 8.52 (br s, 1H, NH).

EXAMPLE W

7

Amino-3-[(1′R,2′S,3′R)-4′-hydroxymethyl-2′,3′-dihydroxy-4′-cyclopenten-1-yl]-3H-1,2,3-triazolo[4.5-d]pyrimidine (Formula 25) (8-Azaneplanocin A)

The protected 8-azaneplanocin A (19) (39 mg, 0.1 mmol) was dissolved in 3 mL of CH₂Cl₂ and the resulting solution was cooled to −76° C. Boron trichloride (0.8 mL of a 1M solution in CH₂Cl₂0.8 mmol) was added. The reaction was stirred at −76° C. for 2 h and then allowed to warm to 0° C. before being quenched by the addition of methanol. Removal of the solvents in vacuo followed by the addition and evaporation of a further 40 mL of methanol from the reaction mixture gave a yellow oil. The oil was dissolved in a minimum of ethanol and diluted ten-fold with ethyl acetate to give 10 mg of 25 (38%) as an off-white powder; mp 9295 C (dec); ¹H-NMR (CD₃OD) δ 4.37 (s, 2H, H-6′$_{a,b}$), 4.64 (t, J=5.8 Hz, 1H, H-2′), 4.73 (d, J=5.8 Hz, 1H, H-3′), 5.95 (m, 2H, H-1′and H-5′), 8.48 (s, 1H, H-2); MS (FAB) m/e 265 (HM+), 137 (base+2H).

EXAMPLE X

1-[(1′R,2′S,3′R)-4′-hydroxymethyl-4-′cyclopenten-1′-yl]-2(1H)-pyrimidinone (Formula 26) (CPE-U)

A solution of ≢(1.02 g, 2.78 mmol) in dry dichloromethane (50 mL) was chilled to −78° C. and treated with boron trichloride [10 mL (3.7 equiv.) of a 1 M solution in dichloromethane] and stirred at that temperature for 3 h. The solution was warmed up to 24° C., and quenched with methanol (50 ml) and reduced to dryness. This operation was repeated three times. Purification of the residue by flash chromatography (CH₂Cl₂:MeOH, 4:1) gave 205 mg (31%) of pure 26 as a white foam; [α]$^{24}$$_D$ −62° (c 0.47, H₂O); UV (H₂O) max 266 nm (log 4.07); ¹H-NMR (D₂O) δ 4.18 (m, 1H, H-2′), 4.32 (br s, 2H, H-6′$_{a,b}$), 4.62 (d, J=5.5 Hz, 1H, H-3′), 5.52 (m, 1H, H-1′), 5.82 (m, 1H, H-5′), 5.90 (d J=8.0 Hz, 1H, H-5), 7.52 (d, J=8.0 Hz, 1H, H-6); MS (FAB) m/e 241 (MH+).

Biological Activity

CPE-C which has the following formula:

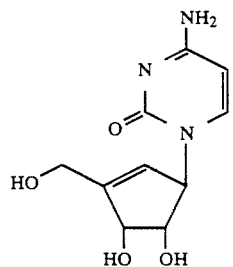

22 was found to be a potent cancer cell differentiating agent. The effect of this compound on differentiation, and nuoleic acid and nucleotide biosynthesis were examined in the malignant human promyelocytic leukemia cell line, HL-60. Continuous exposure for 5 days to 10⁻⁸ to 10⁻⁶M concentrations produced progressive inhibition of cell growth as well as differentiation to a non-malignant phenotype as measured by nitroblue tetrazolium reduction. During this exposure interval, pronounced differentiation to mature myeloid cells occurred wherein 95% of the cell population reduced nitroblue tetrazolium four days after exposure to 10⁻⁷M CPE-C. Preceding differentiation was the inhibition of DNA synthesis which was only 10% of control levels 24 hrs. after exposure to 10⁻⁷M CPE-C, while RNA synthesis was inhibited to a lesser extent. The induction of mature myeloid cells by CPE-C was preceded by the inhibition of c-myc mRNA levels which was more pronounced than the reduction in total cellular RNA synthesis. During the interval of CPE-C treatment, there was a rapid and pronounced inhibition in the level of CTP, but not of UTP, ATP or GTP, where the half-life for the disappearance of CTP was 1.5 to 2 hrs. Following drug removal, cells treated with CPE-C showed a sustained reduction in CTP levels. These results indicate that the reduction in CTP levels leads to rapid inhibition of DNA synthesis and reduction in c-myc levels which precede the appearance of non-malignant, differentiated HL-60 cells. 8-Aza-CPE-A (Formula 25)

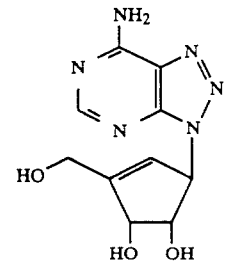

25 displayed significant cytotoxicity against L1210 tumor cells in culture with an IC50 of 3 μM measured after a 48 hour exposure.

The mechanism of action of CPE-C revealed that the cytotoxic effect of the drug was related to the near total abrogation of CTP pools produced in treated cells. Interestingly, this effect showed some tissuespecificity towards the tumor, as ascertained by comparing reduction of CTP levels in both normal and tumor tissue of L1210 bearing mice. Taken together, these results suggested that the CPE-C, or a metabolite of this compounds, inhibited the conversion of UTP to CTP in the reaction catalyzed by CTP synthesase, one of the rate-limiting reactions in the de novo pyrimidine biosynthetic pathways. The reported isolation of the triphosphate metabolite of CPE-C from L1210 cell extracts confirmed that this metabolite was indeed responsible for the inhibition of CTP-synthesase.

In addition to the aforementioned reduction of CTP levels, CPE-C elicited one of the most rapid and complete morphologic responses in myeloid differentiation with the concomitant reduction of c-myc RNA levels preceding the appearance of differentiated cells. The key metabolite responsible for all of these activities appears to be the corresponding triphosphate of CPE-C, CPE-CTP. However, in the course of its metabolic conversion to the triphosphate level, CPE-C also inhibited competitively the phosphorylation of uridine which could contribute in a certain measure to its overall activity. CPE-C also shares a common mechanism of action with carbodine in inhibiting CTP synthesis. Carbodine has a cyclopentane ring without a double bond, and the observed differences in potency between the two compounds suggest that, as with neplanocin A, the unsaturation is a significant factor for increased potency. In reducing CTP levels and inducing differentiation in HL-60 cells, CPE-C was about 100 times more potent than carbodine. A similar potency difference was observed in in vivo antitumor experiments.

Antitumor Activity

Previous in vitro testing against L1210 leukemia indicated that the saturated carbocyclic analogue, carbodine (Formula 27), and its corresponding "ara"-analogue were active, giving an increase in life span values of 82% and 104%, respectively, as reported in *J. Heterocycl. Chem.* 13: 1353, 1976; and *J. Pharm. Sci.* 68: 668, 1979. However, the 2'- and 3'-deoxy analogues as well as the 2',3'-dideoxy analogues of CPE-C were found to be without activity or toxicity, providing further evidence that the activities and toxicities of the carbocyclic compounds described herein cannot be predicted merely from their structural similarity to furanosyl analogues of known activity or toxicity.

The initial CPE-C in vivo tests against the L1210 tumor showed significantly greater levels of activity and potency than carbodine, as shown in Table II. More importantly, experiments using a strain of L1210 leukemia resistant to arabinosyl cytosine (ara-C) indicated that this tumor possessed collateral sensitivity to CPE-C. CPE-C was found to be more effective against the tumor model which was resistant to ara-C than to the normal L1210 model, producing multiple cures against the resistant tumor (cf. Tables II, IV).

Schedule Dependency

TABLE I

Effect of Treatment Schedule on the Activity of CPE-C Against L1210 Leukemia[a]

| CPE-C Treatment Schedule | Optimum Dose (mg/kg/inj) | ILS[b] (%) | LCK[c] |
|---|---|---|---|
| Daily, days 1–9 | 1 | 124 | 3.0 |
| Every 4th day, days 1, 5, 9 | 4 | 91 | 0.1 |
| Every 3 hr × 8, days 1, 5, 9 | 0.5 | 116 | 1.5 |
| None[d] | — | 0 | −3.0 |

[a]Intraperitoneal (IP) implantation of 105 L1210 cells on day zero in CD2F1 mice. IP treatment.
[b]Median percent increase in life span of tumored, treated mice relative to tumored, untreated controls. Control median survival time was 8.9 days. Survival of saline-treated, tumored mice was 9.0 days.
[c]Approximate log cell kill at the end of treatment
[d]Saline treatment, all schedules.

Table II summarizes the antitumor activity of CPE-C against a standard panel of mouse tumor models used by the National Cancer Institute. The compound is both potent and highly active in vivo against L1210 leukemia. Multiple 30-day survivors are obtained at an intraperitoneal dose of 1.0 mg/kg on the QD 1–9 treatment schedule. When administered orally, the activity is somewhat lower, but still significant. Reproducible activity of about 40% ILS is obtained against intracerebral L1210, but the level is so low the effect might be attributed to activity against systemic tumor cells which have metastasized from the brain. CPE-C was inactive against the M5076 sarcoma and showed only modest activity against P388 leukemia. However, a P388 leukemia line resistant to ara-C (P388/ara-C) was collaterally sensitive to CpE-C with multiple long term survivors produced in one experiment.

TABLE II

CPE-C Activity Against Mouse Tumor Models

| Tumor | Tumor Implant Site[b] | Activity[a] | | | | | |
|---|---|---|---|---|---|---|---|
| | | Experiment 1 | | | Experiment 2 | | |
| | | OD[c] | % ILS[d] | LCK[d] | OD | % ILS | LCK |
| L1210 | IP | 1.0 | 212 (4)[e] | >6.0 | 1.0 | 201 (2) | >5.8 |
| | IP[f] | 2.25 | 125 | 1.9 | 2.25 | 57 | −2.2 |
| | SC | 1.5 | 109 | | 1.0 | 83 (1) | |
| | IC | 1.5 | 45 | | 1.0 | 42 | |
| P388 | IP | 1.0 | 88 | 0.9 | 1.5 | 69 | 0.1 |
| P388/ara-C[g] | IP | 1.5 | 165 (3) | >6.5 | 1.5 | 133 | 3.8 |
| M5076 | IP | 0.5 | 5 | −2.0 | | | |

[a]IP, QD1-9 treatment schedule (QD1-13 for M5076).
[b]IP, intraperitoneal; SC, subcutaneous; IC, intracerebral.
[c]Optimum dose (mg/kg/injection).
[d]See abbreviations in Table I.
[e]Number in parenthesis equals number of 30 day surivors out of six mice
[f]Oral drug administration.
[g]Arabinosyl cytosine resistant P388 leukemia.

Since nucleoside antitumor drugs sometimes have a marked treatment schedule dependency, an initial set of experiments was carried out to determine the importance of the treatment schedule for CPE-C. Using intraperitoneally implanted L1210 leukemia, CPE-C was active when given on a chronic (QD 1–9), intermittent (Q4D, D 1,5,9), or on an "around the clock" (Q3H×8, D 1,5,9) schedule, as shown in Table I. Although the intermittent schedule appeared to be slightly less effective than the other two evaluated, no significant schedule dependency was noted. Most of the subsequent tests were conducted using the chronic treatment schedule.

Human Tumor Xenograft Models

CPE-C has good activity against all three of the human tumor xenograft models used in the National Cancer Institute (NCI) tumor panel, tabulated in Table III. Two human solid tumors (1549 lung and MX-1 mammary) grown under the renal capsule of athymic ("nude") mice were sensitive to the compound and tumor regressions were noted in one of the lung tumor experiments, albeit with indications of toxicity. CPE-C was active against the human metastatic melanoma line, LOX, giving about 100% increase in life span against this intraperitoneally implanted model.

TABLE III

CPE-C Activity Against Human Tumor Xenografts in Athymic Mice[a]

| Tumor | Tumor Implant Site[b] | % Tumor Inhibition[c] or (% ILS) | | | |
|---|---|---|---|---|---|
| | | Experiment 1 | | Experiment 2 | |
| | | OD | Activity | OD | Activity |
| A549 Lung | SRC | 1.5 | −59[d] | 2.0 | 92[d] |
| MX-1 Mammary | SRC | 1.5 | 100 | 2.25 | 95 |
| LOX Melanoma | IP | 1.0 | (119) | 2.25 | (80) |

[a]See abbreviations Tables I, II. IP treatment QD1-9.
[b]SRC, subrenal capsule
[c]Based on relative changes in mean tumor weights of treated and control tumors between day 0 and 11. Negative value denotes tumor regression and was calculated by dividing the change in mean treated tumor weight by the initial mean treated tumor weight and multiplying by 100.
[d]This activity associated with weight loss and one or two deaths in each group of six mice.

Comparison with 3-Deazauridine

The biological profile of CPE-C has several similarities to that of 3-deazauridine (3DU). Both compounds are powerful inhibitors of CTP synthesis. Also, tumors resistant to ara-C are collaterally sensitive to 3DU and CPE-C, as shown in Table II. Since the clinical efficacy of 3DU is still under evaluation, an antitumor comparison of these two compounds was conducted to determine whether preclinical advantages exist for CPE-C which might indicate that this compound was worth continued development toward clinical trial. Because the existing 3DU preclinical antitumor data are quite old, and several of the currently used tumor models were not available when 3DU was originally studied, direct comparison evaluations were conducted of 3DU and CPE-C in four preclinical tumor models, as shown in Table IV.

TABLE IV

Antitumor Activitiy Comparison Between CPE-C and 3-Deazauridine[a]

| Tumor | CPE-C | | 3-Deazauridine | |
|---|---|---|---|---|
| | Dose (mg/kg) | % ILS | Dose (mg/kg) | % ILS |
| MX-1 Mammary Xenograft | 2.25 | 100[b] | 300 | 64[b] |
| | 1.5 | 94[b] | 200 | 11[b] |
| LOX Melanoma Xenograft | 2.25 | 80 | 300 | 4 |
| | 1.5 | 58 | 200 | 5 |
| L1210 Leukemia[c] | 2.25 | 146 | 100 | 80 |
| | 1.5 | 171 (2/9)[d] | 50 | 61 |
| | 1.0 | 116 (1/10) | 25 | 72 |
| L1210/ara-C Leukemia[c] | 2.25 | >650 (6/10) | 50 | 166 |
| | 1.5 | >650 (5/9) | 25 | 362 (3/9) |
| | 1.0 | >650 (6/10) | 12.5 | >650 (9/10) |

[a]QD1-9 treatment schedule. MX-1 subrenal capsule tumor implant site, all others intraperitoneal. Compounds tested in the same experiment.
[b]% tumor weight inhibition for this solid tumor based on changes in tumor weights on day 0 and day 11.
[c]Experiment terminated on day 60 rather than the normal day 30. When >50% of the tumored animals were alive on day 60, the median survival time was not reached.
[d]Numbers in parenthesis are number of 60 day survivors per test group.

In the MX-1 human mammary solid tumor xenograft system, CPE-C was very effective, giving complete inhibition of tumor growth relative to untreated controls. 3DU was inactive according to established NCI criteria. Against the human LOX melanoma xenograft, 3DU was, again, inactive with a three-log10 increase in tumor burden observed at the end of treatment. In contrast, CPE-C was active in producing an ILS of 80% at an optimum dose of 2.25 mg/kg on the QD 1-9 treatment schedule. This resulted in a two-log tumor cell kill and, therefor, a five-log difference in tumor burden between CPE-C and 3DU as the result of drug treatment. CPE-C was about 100 times more potent than 3DU in both xenograft experiments.

Because CPE-C was so active against ara-C resistant P388 leukemia, and the reported activity of CPE-C and 3DU against L1210/ara-C, the two compounds were directly compared in the sensitive and ara-C resistant L1210 models (Table IV). Although 3DU was active in the standard L1210 leukemia system (80% ILS at 100 mg/kg), CPE-C was significantly better in this "head to head" comparison, producing multiple long term survivors at 1.5 mg/kg, consistent with the results shown in Table II. Against L1210/ara-C, however, both 3DU and CPE-C were very active, giving multiple 60-day survivors at more than one dose. In this model, there was essentially no difference between CPE-C and 3DU other than the usual greater potency of CPE-C.

Antiviral Activity

Carbodine (Formula 27), was shown to be very effective against several viruses, and in particular influenza viruses, cf. *J. Med. Chem.* 29: 1720, 1986 and *Antimicrob. Agents and Chemother.* 20: 769, 1981. Slight carbodine activity was noted against rhinovirus 1A, respiratory syncytial virus (RSV), and two other RNA viruses. Good activity, however, was noted against several DNA viruses. Carbodine was found to be more potent against a strain of the HSV-1 virus deficient in its ability to induce thymidine kinase in the host cell (TK−) than a strain which induces this enzyme (TK+). However, it is possible that experimental parameters (e.g., host cell type, virus strain, and the like, may influence carbodine's activity against HSV-1 TK−.

CPE-C shows significant activity in several DNA viral systems as measured by its ability to inhibit viral cytopathic effects, shown in Table V. CPE-C potency and activity [measured by its virus rating (VR)] are greater than arabinosyl adenine (ara-A) against both the TK− and TK+ strains of HSV-1. Acyclovir is more active that CPE-C against the TK+ strain, but it is inactive against the non-enzyme inducing strain (TK−), since thymidine kinase is required to activate acyclovir. A similar profile is observed against HSV-2, cf. Table V.

A fourth DNA virus, vaccinia, is very sensitive to CPE-C (Table V). The carbocyclic nucleoside is not only more active than the positive control compound, ara-A, but also is about 100 times more potent. CPE-C is also active against this virus in vivo in the tail pox mouse model [Boyle et al., *Antimicro. Agents Chemo-* ther.-1966, 536 (1967)]. At 1.5 mg/kg (QD-1 to 6), CPE-C provided good protection against the pathogenic effects of the vaccinia virus (Table VIII).

TABLE VIII

Antiviral Activity of CPE-C
(Murine Vaccinia Tailpox Model)

| PBS Control[a] Pox Count | Ara-A Dose[b] (mg/kg) | Pox Count[c] | CPE-C Dose[b] (mg/kg) | Pox Count[c] |
|---|---|---|---|---|
| 45.8 | 300 | 2.8 | 1.5 | 0.8 |

[a]Diluent-treated mice (phosphate buffer saline) challenged with the virus
[b]QD 1-7 started on the day preceding virus challenge
[c]Mean value (20 mice)

TABLE V

Evaluation of CPE-C Against DNA Viruses[a,b]

| Virus | Strain | CPE-C VR | ID$_{50}$ ($\mu$g/ml) | Positive Control Compound | VR | ID$_{50}$ ($\mu$g/ml) |
|---|---|---|---|---|---|---|
| Herpes simplex type 1 | E-377 (TK+)[c] | 3.8 | 0.3 | Ara-A | 1.8 | 13.6 |
|  |  |  |  | Acyclovir | 6.7 | 0.7 |
| Herpes simplex type 1 | HF (TK−)[c] | 3.8 2.7 | 0.6 1.3 | Ara-A | 3.3 2.9 | 2.1 1.9 |
| Herpes simplex type 2 | MS | 2.3 | 2.7 | Ara-A | 1.3 | 49.9 |
|  |  |  |  | Acyclovir | 4.5 | 5.3 |
| Vaccinia | Lederle CA | 4.6 | 0.1 | Ara-A | 3.1 | 9.8 |

[a]The antiviral activity of each compound is expressed as a virus rating (VR), and the potency is given as an ID$_{50}$. The VR is a weighted measurement of antiviral activity that takes into account both the degree of inhibition of virus-induced cytopathogenic effects and the degree of cytotoxicity produced by the test compound (see Experimental Section). The ID$_{50}$ is the concentration of the test compound in $\mu$g/ml required to inhibit the virus-induced cytopathogenic effects by 50%.
[b]Vero cells (African green monkey kidney cells) were host cells in all experiments.
[c]HSV-1 strain E-377 induces thymidine kinase in host cells. Strain HF does not induce this enzyme.

Table VI compares the activity of CPE-C with DHPG against cytomegalovirus and varicella-zoster using reduction of virus yield and percent plaque reductions as respective endpoints. Activity was observed for both compounds, but the positive control (DHPG) was superior.

TABLE VI

Evaluation of CPE-C Against Cytomegalovirus and Varicella-Zoster Virus

| Concentration ($\mu$g/ml) | Cytomegalovirus[a] Reduction in Virus Yield (log PFU/ml)[b] | | Vericella-Zoster[a] Plaque Reduction[b] (%) | |
|---|---|---|---|---|
|  | CPE-C | DHPG[c] | CPE-C | DHPG |
| 320 | 5.3[d] | 5.3[e] | 36[d] | 100[d] |
| 100 | 2.0[e] | 5.3[f] | 41[e] | 100[f] |
| 32 | 2.0[e] | 5.3 | 36[e] | 85 |
| 10 | 1.9[e] | 3.8 | 33[f] | 69 |
| 3.2 | 1.5[e] | — | 33 | 46 |
| 1.0 | 1.4[e] | 1.1 | 36 | 44 |
| 0.32 | 1.3[f] | — | 33 | — |
| 0.1 | 0.8 | — | 21 | — |
| 0.032 | — | — | 3 | — |
| 0.01 | — | — | 0 | — |

[a]CMV strain AD 169. The host cell line is MRC5 (diploid human embryonic lung cells). VZV isolate DM625. The host cell line is Huf (humal diploid foreskin cells in monolayer culture).
[b]See Experimental Section.
[c]9-(1,3-Dihydroxy-2-propoxymethyl)guanine
[d]Slightly toxic based on gross cell morphology.
[e]Very slightly toxic CPE-C has significant activity against a spectrum of RNA viruses in vitro, as shown in Table VII. Virus ratings greater than two were obtained against vesicular stomatitis virus, Punta Toro virus and the Hong Kong influenza virus. In the Japanese encephalitis virus system, CPE-C has a VR of 2.4, with a greater potency and higher therapeutic index than Ribavarin, the positive control compound. Activity was not seen against Rhinovirus 1A. No anti-HIV (retroviral) activity was observed using the Mitsuya and Broder assay, and potent cytotoxicity to the ATH8 host cell line was noted.

In addition U.S. Army testing, (USAMRIID, Fort Detrick, Md.) CPE-C was particularly active against the Rift Valley Fever virus.

TABLE VII

Evaluation of CPE-C Against RNA Viruses[a,b]

| Virus | Strain | Host Cell[c] | CPE-C VR | ID$_{50}$[d] ($\mu$g/ml) | TI[e] | Positive Control Compound | VR | ID$_{50}$ ($\mu$g/ml) | TI |
|---|---|---|---|---|---|---|---|---|---|
| Vesicular Stomatitis | Indiana | L929 | 2.4 3.0 | 0.57 0.25 | 0.6 0.4 | 3-Deaza- aristeromycin | 2.1 3.0 | 4.3 2.0 | 2.3 1.6 |
| Yellow Fever | Asibi | Vero | 0.9 | 5.05 | 0.1 | Selenazole | 2.4 | 1.8 | 0.6 |
| Janapese Encephalitis | Najayama | Vero | 2.4 | 0.10 | 3.1 | Ribavirin | 2.4 | 3.0 | 1.1 |
| Punta Toro | Adames | Vero | 1.5 | 1.01 | 0.3 | Ribavirin | 1.8 | 20.1 | 5.0 |
| Influenza | A2/Aichi/2/68 | MDCK | 2.4 | 18.2 | ND | Ribavirin | 3.6 | 18.7 | ND |

TABLE VII-continued

| | | | Evaluation of CPE-C Against RNA Viruses[a,b] | | | | | | |
|---|---|---|---|---|---|---|---|---|---|
| | | | | CPE-C | | | Positive Control | | |
| Virus | Strain | Host Cell[c] | VR | $ID_{50}$[d] ($\mu$g/ml) | TI[e] | Compound | VR | $ID_{50}$ ($\mu$g/ml) | TI |
| (Hong Kong) | | | | | | | | | |

[a]See Table I for definitions.
[b]Data obtained from the USAMRIID antiviral testing program[33] except for Influenza which was obtained under an NCI purchase order (see Experimental Section). USAMRIID virus rating values, calculated by the method of Hoffman and Sidwell[35] were converted to Ehrlich values[34] for consistency by multiplication by three.
[c]L929 cells are normal mouse fibroblasts. MDCK cells are Madin-Darby canine kidney cells.
[d]Concentration of the drug that causes a 50% reduction in virus replication.
[e]Therapeutic index equals minimum toxic drug concentration (concentration causing 50% reduction in % survival of host cells) divided by the $ID_{50}$ for the drug.

Antitumor Evaluations

In vivo antitumor tests were conducted according to established NCI protocols. Tumor cells were implanted at the specified sites and treatment was initiated 24 hours later. Drugs were administered intraperitoneally in physiologic saline vehicle and their effects were evaluated at several dosage levels in each experiment. Life span experiments were terminated on day 30 unless otherwise noted. Subrenal capsule assays were evaluated on day 11. Long term survivors are included in the % ILS calculations. When activity was observed in an initial test, a minimum of one confirmatory test was conducted, normally at a different testing laboratory. In the instance of the direct comparison of CPE-C and 3-deazauridine (3DU) against L1201/ara-C, only one experiment was conducted because of existing 3DU data.

It has been well established that all tumor models do not have similar sensitivity to either established or new anticancer drugs. Rather, a broad spectrum of tumor sensitivity has been observed. At one end of the scale of sensitive tumors are tumors such as Ehrlich ascites, Dunning leukemia, and Walker 256 carcinoma, which tumors are far too sensitive to be useful as animal models for predicting activity in humans. These tumor models were abandoned many years ago because they gave too many false positives as clinical candidates. On the other end of the spectrum are certain human tumors such as lung and colon xenografts, and mouse tumors such as mammary 3CDJ2 and Lewis lung- 3LL39. Such a small percentage of compounds were active against these refractory tumor models that they have been determined to be too expensive for use in a primary screening system. These models are currently used for testing only after activity is discovered in one of the other more sensitive tumor models. L1210 leukemia is one of the more sensitive tumor models which continues to be used as a primary screening tumor.

In addition to the tremendous differences in drug sensitivity between L1210 leukemia and the xenografts, there are also significant differences in the form and manner in which the tumors are used for testing. L1210 leukemia is an ascites fluid mouse tumor which is injected into the peritoneal cavity of a mouse having a normal immune system. In contrast, all three xenografts are surgically implanted solid, human tumor pieces. Special immune-suppressed nude mice are anesthetized, cut open, the solid tumor fragment is implanted beneath the renal capsule, and the wound is closed. The vast differences between the L1210 and xenograft systems are reflected in the costs attendant on testing a compound in each model. It costs more than six times as much to test a compound in a single human xenograft system as it does to test the same compound against L1210 leukemia.

Thus it is clear that mouse L1210 leukemia, which is a liquid, and the solid human tumor xenografts have large differences in drug sensitivity, tumor test characteristics, and cost. However, if it is known that a compound had activity against L1210 leukemia, there is no reasonable probability that anyone skilled in the art would predict that this compound would also have activity against all three of the human tumor xenograft models in the NCI tumor panel. In *Advances in Pharmacology and Chemotherapy* 20:1-20, the results of preclinical antitumor screening in vivo is described for the years 1976-1982. Alternative tumor panel models were used to uncover new agents that were not selected by L1210 and there cannot be a direct correlation of responsiveness based on tumor histology or tissue of origin. There is no apparent positive correlation between efficacy in a preclinical model and clinical utility based on tumor type.

Antiviral Evaluations

Cytopathogenic Inhibition Test

Mammalian cells were pregrown as monolayer cultures in wells of COSTAR 96-well tissue culture plates using suitable cell culture media. Stock viruses were pretitered and diluted in cell culture medium to yield 32 CCID50 (Cell culture infectious dose, 50%), unites per 0.1 ml. Antiviral assays were designed to test a minimum of seven concentrations of each compound from cytotoxic to noncytotoxic levels against each of the challenge viruses in triplicate, in microtiter plate wells containing suitable host cell monolayers. To each of the replicate cell cultures was added 0.1 ml of the test drug solution and 0.1 ml of virus suspension. Cell control containing cells plus medium, virus controls containing cells plus medium plus virus, and drug cytotoxicity controls containing cells plus each drug in medium were run simultaneously with the test sample assayed in each experiment. The covered plates were incubated at 37° C. in a humidified atmosphere containing 2% $CO_2$ and then examined microscopically for virus-induced cytopathogenic effects (CE) at 3-4 days postvirus inoculation. Antiviral activity was determined by calculating the degree of inhibition of virus-induced CE in drug-treated, virus-infected cell cultures by means of a virus rating (VR). The VR is a standard weighted measurement of antiviral activity taking into account both the degree of CE inhibition and drug cytotoxicity, and is determined by a modification of the method of Erlich et al., Ann. N.Y. Acad. Sci. 130: 5, 1975.

The VR was calculated as 0.1 of the sum of the numerical differences between the recorded CE grade of each test well and that of the corresponding virus control in the culture plate. Drug cytotoxicity was determined by gross morphological changes in the cell monolayers observed by microscopic examination. Numerical differences between the reading of test wells containing a drug concentration which was partially cytotoxic (cell monolayer intact) and their corresponding virus controls were halved.

Experience has shown that a VR of 1.0 or greater is indicative of significant antiviral activity with a high degree of reproducibility in confirmatory in vitro tests. Compounds with a VR of 1.0 or greater are therefore considered active. A compound with a VR of 0.5–0.9 is considered to have possible or marginal activity, and any compound with a VR of less than 0.5 is considered to be inactive in the test system. The $ID_{50}$ (dose required to inhibit virus-induced CE by 50%) is also determined.

Cytomegalovirus (CMV) Yield Reduction Assay

Subfluent monolayers of MRC5 cells, grown in 35 mm wells of Falcon 6-well tissue culture plates, were rinsed with phosphate-buffered saline (PBS) and exposed to 0.5 ml of virus diluted in Eagle's MEM+2% fetal bovine serum to a multiplicity of infection of 0.2 PFU/cell) for 1.5 hours at 37° C. The virus inocula were removed after adsorption and the infected cell layers were rinsed with PBS. Duplicate infected cell layers were fed with 2.0 ml aliquots of each drug concentration (dissolved and diluted in MEM+2% FBS). Untreated, infected controls and cell controls were fed with medium. Uninfected drug-treated cell cultures served as cytotoxicity controls. The cultures were incubated at 37° C. in a humidified atmosphere containing 2% $CO_2$. On day 3 post-infection, the fluids were aspirated and replaced with fresh drug and/or medium. The cell monolayers were examined microscopically on day 6 for viral CE and harvested as follows: The cultures were frozen and thawed to disrupt the cells. The cellular material was scraped into the ambient medium, and the contents from replicate cultures were pooled, dispensed into cryotubes, and stored in liquid nitrogen.

The harvested samples were thawed and titrated for infectious virus yield by the following plaque assay procedure. Subconfluent cell monolayer cultures pregrown in 16 mm 12-well tissue culture plates were rinsed with PBS and exposed to 0.25 ml aliquots of harvested virus suspension for 1.5 hours at 37° C. in a humidified atmosphere of 2% C02 in air. The virus inocula were removed after adsorption, and the infected cell layers were rinsed with PBS. Triplicate virus-infected cell layers were overlaid with each drug concentration contained in 1 ml of medium (MEM +2% FBS in 0.25% agarose). Untreated virus-infected cell controls, drug cytotoxicity controls (sham-infected cell monolayer cultures overlaid with drug-containing medium), and cell culture controls were included. The tissue culture plates were incubated 17 37° C. in the $CO_2$ incubator for 5–6 days, until discrete well-defined foci (plaques) of viral CE were formed. The cell layers were fixed with 10% buffered formalin and stained with 0.03% methylene blue. The plates were examined microscopically and the plaques were counted under low magnification. Antiviral activity was measured by comparing the mean number of plaques from triplicate drug-treated, virus-infected cell cultures with the mean number of plaques in 5teh untreated virus control cultures. Any reduction in the mean number of plaques present in drug-treated, virus-infected cell cultures, when compared with the mean number of plaques in the virus-infected control cultures, was expressed as percent reduction. The minimum drug concentration that reduced the mean plaque number by 50% ($ID_{50}$) was calculated by using a regression analysis program for semilog curve fitting.

Varicella-Zoster Virus (VZV) Plaque Reduction Assay

The plaque reduction assay procedure for VZV was the same as that used to titrate samples form the CMV yield assay, except that the VAV virus inocula were not removed after a one-hour virus adsorption period. Agarose was omitted from the drug-containing overlay medium. The VZV-infected human foreskin cell monolayer cultures were fed with fresh drug and medium after 72 hours incubation and returned to the incubator. The discrete foci of CE (Plaques) were counted six days post-virus inoculation.

Dose, Route of Administration and Formulation

Vaccinia Tailpox model. This in vivo vaccinia virus model was developed by Boyle et al. and further refined by Joshi et al. Mice inoculated in the tail vein with virus develop dermal lesions over the entire tail surface. These lesions are enumerated after fluorescence staining and are a function of viral dose, animal weight and inoculation distance from the base of the tail. The IHD strain of vaccinia virus, passed once in mouse brain and once in primary rabbit kidney culture, was used. Random bred Swiss mice (CD-I, VAF+, Charles River Laboratories, Inc.), weighing 18–21 g, were inoculated via the tail vein (1 cm from the base) with 0.2 mL of a 1:40 dilution of the virus suspension. Compounds were administered subcutaneously once daily for 7 days with the first dose given the day preceding virus challenge. The positive control drug, ara-A, was administered at 300 mg/kg/day. CPE-C was administered at 1.5 mg/kg/day or 1.0 mg/kg/day. Drug-diluent control mice received phosphate buffered saline (PBS, pH 7.2). Uninfected drug-treated toxicity controls were included for each treatmentaadministered. Animals were sacrificed on the sixth day and their tails were stained with a solution of 1% fluorescein-0.5% methylene blue in 70% methanol. Lesions were enumerated under UV light (354 nm) with the aid of a hand lens. The average number of lesions for each treatment group was calculated prior to, and following square root transformation or the individual tailpox counts. Tailpox counts from each treatment group were statistically compared by Student's T-test.

The compounds of the present invention can be administered to patients suffering from cancer and viral diseases, including AIDS, at doses ranging from about 0.01 to about 10 mg/kg/day total dosage. The drugs may be administered orally or intravenously, or by other convenient routes.

The compounds of the present invention can be combined with a pharmaceutically acceptable carrier therefore, and optionally other therapeutic and/or prophylactic ingredients. The carriers must be "acceptable" in the sense of being compatible with the other ingredients of the formula, and not deleterious to the recipient thereof.

In addition to the active ingredients according to the present invention, pharmaceutical compositions to be used in treating cancer and viral diseases according to the present invention include compositions wherein the active ingredient is contained in an effective amount to achieve its intended purpose. Determination of the effective amounts is within the purview of one skilled in the art.

In addition to the cyclopentenyl pyrimidines of the present invention, these pharmaceutical compositions may contain suitable pharmaceutically acceptable carriers comprising excipients and auxiliaries which facilitate processing of the active ingredients into preparations which can conveniently be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 5 to about 85 percent by weight, of active ingredient, along with the excipient.

The compositions of the present invention can also be administerei intranasally or buccally. Administration across the mucous membranes provides more rapid uptake of the compounds into the bloodstream that administration orally, and any possible destruction by stomach acids is eliminated.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets or dragee cores.

Suitable excipients are, in particular, fillers such as sugars, for example, lactose, sucrose, mannitol, or sorbitol; cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, alginic acid, or a salt thereof, such as sodium alginate. Auxiliaries are, above all, flow-regulating agents and lubricants, for example, silica talc, stearic acid or salts thereof such as magnesium stearate or calcium stearate, and/or polyethylene glycol. Dragee cores are provided with suitable coatings which, if desired, can be resistant to gastric juices. For this purpose, concentrated sugar solutions may be used, which may optionally contain gum arabic, talc, polyvinyl pyrrolidone, polyethylene glycol and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils, liquid paraffin, or liquid polyethylene glycols. In addition, other stabilizers may be used.

Pharmaceutical preparations which can be administered rectally include, for example, suppositories, which consist of a combination of the active compounds with a suppository base. Suitable suppository bases are, for example natural or synthetic triglycerides, paraffin hydrocarbons, polyethylene glycols, or higher alkanols. In addition, it is also possible to use gelatin rectal capsules which consist of a combination of the active compounds with a base. Possible base materials include liquid triglycerides, polyethylene glycols, or paraffin hydrocarbons.

Suitable formulations for parenteral administration include aqueous solutions of the active compounds in water-soluble forms, for example, water-soluble salts. In addition, suspensions of the active compounds as appropriate oily injection suspensions may be administered. Suitable lipophilic solvents or vehicles include fatty oils, such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension may also contain stabilizers.

Another method for administering the compounds of the present invention includes the use of liposomes, pharmaceutical compositions in which the active ingredient is contained either dispersed or variously present in corpuscles consisting of aqueous concentric layers adherent to lipidic layers (hydrophobic). The drug may be present both in the aqueous layer and in the lipidic one (inside or outside) or, in any event, in the non-homogeneous system generally known as a liposomic suspension.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method of treating cancer comprising administering to a patient an anticancer effective amount of the compound 4-amino-1-[(1'R,2'S,3'R)-2',3'-dihydroxy-4'-hydroxymethyl-4'-cyclopenten-1'-yl]-2(1H)pyrimidinone, and wherein the cancer is chosen from the group consisting of lung cancer, breast cancer, colon cancer and melonoma.

2. A method of treating viral diseases comprising administering to a patient an antiviral effective amount of the compound 4-amino-1[(1′R,2′S,3′R)-2′,3′-dihydroxy-4′-hydroxymethyl-4′-cyclopenten-1′-yl]-2(2H)pyrimidinone, and wherein the viral disease is caused by a virus selected from the group consisting of herpes simplex-I virus, herpes simples-II virus, vaccinia virus, cytomegalovirus, varicella-zoster virus, vesicular stomatitis virus, Punta Toro virus, influenza viruses, Japanese Encephalitis virus and the Rift Valley Fever Virus.

* * * * *